US012023036B2

(12) United States Patent
Wedul et al.

(10) Patent No.: US 12,023,036 B2
(45) Date of Patent: Jul. 2, 2024

(54) OCCLUSIVE MEDICAL DEVICE HAVING SENSING CAPABILITIES

(71) Applicant: BOSTON SCIENTIFIC SCIMED, INC., Maple Grove, MN (US)

(72) Inventors: Eric Wedul, Minneapolis, MN (US); Jan-Hung Chen, St. Paul, MN (US); Harishankar Natesan, Shoreview, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 17/554,673

(22) Filed: Dec. 17, 2021

(65) Prior Publication Data
US 2022/0192677 A1    Jun. 23, 2022

Related U.S. Application Data

(60) Provisional application No. 63/127,573, filed on Dec. 18, 2020.

(51) Int. Cl.
*A61B 17/12*   (2006.01)
*A61B 5/00*    (2006.01)
*A61B 17/00*   (2006.01)

(52) U.S. Cl.
CPC ...... *A61B 17/12122* (2013.01); *A61B 5/6869* (2013.01); *A61B 17/12172* (2013.01);
(Continued)

(58) Field of Classification Search
CPC ........ A61B 17/12122; A61B 17/12172; A61B 5/6869; A61B 2017/00632;
(Continued)

(56) References Cited

U.S. PATENT DOCUMENTS 1,782,830 A    6/1876    French
1,967,318 A    10/1931   Monahan
(Continued)

FOREIGN PATENT DOCUMENTS

CN    106859722 A    6/2017
WO      9313712 A1    7/1993
(Continued)

OTHER PUBLICATIONS

International Search Report and Written Opinion dated Mar. 30, 2022 for International Application No. PCT/US2021/064094.
(Continued)

*Primary Examiner* — Katherine M Shi
*Assistant Examiner* — Mohammed S Adam
(74) *Attorney, Agent, or Firm* — Seager, Tufte & Wickhem LLP

(57) ABSTRACT

Example occlusive implants are disclosed. An example occlusive implant includes an expandable framework configured to shift between a collapsed configuration and an expanded configuration, an occlusive member disposed along at least a portion of the expandable framework and a first collar attached to the expandable framework. The occlusive implant also includes a sensor housing coupled to the first collar, the sensor housing having a first end and a second end opposite the first end and a second collar slidably disposed along an outer surface of the sensor housing. Further, the second collar is coupled to the expandable framework via a spring. The occlusive implant also includes a sensor disposed along the second end of the sensor housing.

20 Claims, 11 Drawing Sheets

(52) U.S. Cl.
CPC ............... *A61B 2017/00632* (2013.01); *A61B 2017/1205* (2013.01)

(58) Field of Classification Search
CPC ........ A61B 17/12022; A61B 17/12031; A61B 17/12036; A61B 17/1204; A61B 17/12045
See application file for complete search history.

(56) References Cited

U.S. PATENT DOCUMENTS

| | | |
|---|---|---|
| 3,402,710 A | 9/1968 | Paleschuck |
| 3,540,431 A | 11/1970 | Mobin-Uddin |
| 3,638,652 A | 2/1972 | Kelley |
| 3,844,302 A | 10/1974 | Klein |
| 3,874,388 A | 4/1975 | King |
| 4,007,743 A | 2/1977 | Blake |
| 4,309,776 A | 1/1982 | Berguer |
| 4,341,218 A | 7/1982 | U |
| 4,364,392 A | 12/1982 | Strother et al. |
| 4,545,367 A | 10/1985 | Tucci |
| 4,585,000 A | 4/1986 | Hershenson |
| 4,603,693 A | 8/1986 | Conta et al. |
| 4,611,594 A | 9/1986 | Grayhack et al. |
| 4,619,246 A | 10/1986 | Molgaard-Nielsen et al. |
| 4,638,803 A | 1/1987 | Rand |
| 4,665,906 A | 5/1987 | Jervis |
| 4,681,588 A | 7/1987 | Ketharanathan |
| 4,710,192 A | 12/1987 | Liotta et al. |
| 4,793,348 A | 12/1988 | Palmaz |
| 4,832,055 A | 5/1989 | Palestrant |
| 4,917,089 A | 4/1990 | Sideris |
| 4,921,484 A | 5/1990 | Hillstead |
| 5,037,810 A | 8/1991 | Saliba, Jr. |
| 5,041,090 A | 8/1991 | Scheglov et al. |
| 5,041,093 A | 8/1991 | Chu |
| 5,042,707 A | 8/1991 | Taheri |
| 5,053,009 A | 10/1991 | Herzberg |
| 5,064,435 A | 11/1991 | Porter |
| 5,071,407 A | 12/1991 | Termin et al. |
| 5,078,736 A | 1/1992 | Behl |
| 5,098,440 A | 3/1992 | Hillstead |
| 5,108,420 A | 4/1992 | Marks |
| 5,116,360 A | 5/1992 | Pinchuk et al. |
| 5,122,136 A | 6/1992 | Guglielmi et al. |
| 5,171,259 A | 12/1992 | Inoue |
| 5,176,692 A | 1/1993 | Wilk et al. |
| 5,192,301 A | 3/1993 | Kamiya et al. |
| 5,234,458 A | 8/1993 | Metais |
| 5,256,146 A | 10/1993 | Ensminger et al. |
| 5,258,000 A | 11/1993 | Gianturco |
| 5,258,042 A | 11/1993 | Mehta |
| 5,284,488 A | 2/1994 | Sideris |
| 5,304,184 A | 4/1994 | Hathaway et al. |
| 5,306,234 A | 4/1994 | Johnson |
| 5,334,217 A | 8/1994 | Das |
| 5,350,398 A | 9/1994 | Pavcnik et al. |
| 5,350,399 A | 9/1994 | Erlebacher et al. |
| 5,353,784 A | 10/1994 | Nady-Mohamed |
| 5,366,460 A | 11/1994 | Eberbach |
| 5,366,504 A | 11/1994 | Andersen et al. |
| 5,370,657 A | 12/1994 | Irie |
| 5,375,612 A | 12/1994 | Cottenceau et al. |
| 5,397,355 A | 3/1995 | Marin et al. |
| 5,409,444 A | 4/1995 | Kensey et al. |
| 5,417,699 A | 5/1995 | Klein et al. |
| 5,421,832 A | 6/1995 | Lefebvre |
| 5,425,744 A | 6/1995 | Fagan et al. |
| 5,433,727 A | 7/1995 | Sideris |
| 5,443,454 A | 8/1995 | Tanabe et al. |
| 5,443,478 A | 8/1995 | Purdy |
| 5,451,235 A | 9/1995 | Lock et al. |
| 5,464,408 A | 11/1995 | Duc |
| 5,469,867 A | 11/1995 | Schmitt |
| 5,490,856 A | 2/1996 | Person et al. |
| 5,522,790 A | 6/1996 | Moll et al. |
| 5,522,822 A | 6/1996 | Phelps et al. |
| 5,522,836 A | 6/1996 | Palermo |
| 5,527,322 A | 6/1996 | Klein et al. |
| 5,527,338 A | 6/1996 | Purdy |
| 5,569,204 A | 10/1996 | Cramer |
| 5,591,196 A | 1/1997 | Marin et al. |
| 5,614,204 A | 3/1997 | Cochrum |
| 5,634,936 A | 6/1997 | Linden et al. |
| 5,634,942 A | 6/1997 | Chevillon et al. |
| 5,637,097 A | 6/1997 | Yoon |
| 5,643,282 A | 7/1997 | Kieturakis |
| 5,643,292 A | 7/1997 | Hart |
| 5,649,953 A | 7/1997 | Lefebvre |
| 5,653,690 A | 8/1997 | Booth et al. |
| 5,662,671 A | 9/1997 | Barbut et al. |
| 5,669,933 A | 9/1997 | Simon et al. |
| 5,681,347 A | 10/1997 | Cathcart et al. |
| 5,690,671 A | 11/1997 | McGurk et al. |
| 5,693,067 A | 12/1997 | Purdy |
| 5,695,525 A | 12/1997 | Mulhauser et al. |
| 5,700,285 A | 12/1997 | Myers et al. |
| 5,702,421 A | 12/1997 | Schneidt |
| 5,709,224 A | 1/1998 | Behl et al. |
| 5,709,704 A | 1/1998 | Nott et al. |
| 5,709,707 A | 1/1998 | Lock et al. |
| 5,725,552 A | 3/1998 | Kotula et al. |
| 5,725,568 A | 3/1998 | Hastings |
| 5,733,294 A | 3/1998 | Forber et al. |
| 5,733,302 A | 3/1998 | Myler et al. |
| 5,735,290 A | 4/1998 | Sterman et al. |
| 5,749,883 A | 5/1998 | Halperin |
| 5,749,894 A | 5/1998 | Engelson |
| 5,766,219 A | 6/1998 | Horton |
| 5,769,816 A | 6/1998 | Barbut et al. |
| 5,776,097 A | 7/1998 | Massoud |
| 5,782,860 A | 7/1998 | Epstein et al. |
| 5,785,679 A | 7/1998 | Abolfathi et al. |
| 5,800,457 A | 9/1998 | Gelbfish |
| 5,800,512 A | 9/1998 | Lentz et al. |
| 5,810,874 A | 9/1998 | Lefebrve |
| 5,823,198 A | 10/1998 | Jones et al. |
| 5,830,228 A | 11/1998 | Knapp et al. |
| 5,836,913 A | 11/1998 | Orth et al. |
| 5,836,968 A | 11/1998 | Simon et al. |
| 5,843,118 A | 12/1998 | Sepetka et al. |
| 5,846,260 A | 12/1998 | Maahs |
| 5,846,261 A | 12/1998 | Kotula et al. |
| 5,849,005 A | 12/1998 | Garrison |
| 5,851,232 A | 12/1998 | Lois |
| 5,853,422 A | 12/1998 | Huebsch et al. |
| 5,855,597 A | 1/1999 | Jayaraman |
| 5,865,802 A | 1/1999 | Yoon et al. |
| 5,865,791 A | 2/1999 | Whayne et al. |
| 5,868,708 A | 2/1999 | Hart et al. |
| 5,876,367 A | 3/1999 | Kaganov et al. |
| 5,879,366 A | 3/1999 | Shaw et al. |
| 5,882,340 A | 3/1999 | Yoon |
| 5,885,258 A | 3/1999 | Sachdeva et al. |
| 5,891,558 A | 4/1999 | Bell et al. |
| 5,895,399 A | 4/1999 | Barbut et al. |
| 5,904,680 A | 5/1999 | Kordis et al. |
| 5,904,703 A | 5/1999 | Gilson |
| 5,906,207 A | 5/1999 | Shen |
| 5,910,154 A | 6/1999 | Tsugita et al. |
| 5,911,734 A | 6/1999 | Tsugita et al. |
| 5,916,236 A | 6/1999 | Muijs Van de Moer et al. |
| 5,928,192 A | 7/1999 | Maahs |
| 5,928,260 A | 7/1999 | Chin et al. |
| 5,935,145 A | 8/1999 | Villar et al. |
| 5,935,147 A | 8/1999 | Kensey et al. |
| 5,935,148 A | 8/1999 | Villar et al. |
| 5,941,249 A | 8/1999 | Maynard |
| 5,944,738 A | 8/1999 | Amplatz et al. |
| 5,947,997 A | 9/1999 | Pavcnik et al. |
| 5,951,589 A | 9/1999 | Epstein et al. |
| 5,951,599 A | 9/1999 | McCrory |
| 5,954,694 A | 9/1999 | Sunseri |
| 5,957,940 A | 9/1999 | Tanner et al. |

(56) References Cited

U.S. PATENT DOCUMENTS

| | | |
|---|---|---|
| 5,961,545 A | 10/1999 | Lentz et al. |
| 5,976,174 A | 11/1999 | Ruiz |
| 5,980,514 A | 11/1999 | Kupiecki et al. |
| 5,980,555 A | 11/1999 | Barbut et al. |
| 5,989,281 A | 11/1999 | Barbut et al. |
| 5,993,469 A | 11/1999 | McKenzie et al. |
| 5,993,483 A | 11/1999 | Gianotti |
| 5,997,557 A | 12/1999 | Barbut et al. |
| 6,004,348 A | 12/1999 | Banas et al. |
| 6,007,523 A | 12/1999 | Mangosong |
| 6,007,557 A | 12/1999 | Ambrisco et al. |
| 6,010,517 A | 1/2000 | Baccaro |
| 6,010,522 A | 1/2000 | Barbut et al. |
| 6,013,093 A | 1/2000 | Nott et al. |
| 6,024,754 A | 2/2000 | Engelson |
| 6,024,755 A | 2/2000 | Addis |
| 6,024,756 A | 2/2000 | Huebsch et al. |
| 6,027,520 A | 2/2000 | Tsugita et al. |
| 6,033,420 A | 3/2000 | Hahnen |
| 6,042,598 A | 3/2000 | Tsugita et al. |
| 6,048,331 A | 4/2000 | Tsugita et al. |
| 6,051,014 A | 4/2000 | Jang |
| 6,051,015 A | 4/2000 | Maahs |
| 6,056,720 A | 5/2000 | Morse |
| 6,063,070 A | 5/2000 | Eder |
| 6,068,621 A | 5/2000 | Balceta et al. |
| 6,074,357 A | 6/2000 | Kaganov et al. |
| 6,076,012 A | 6/2000 | Swanson et al. |
| 6,079,414 A | 6/2000 | Roth |
| 6,080,182 A | 6/2000 | Shaw et al. |
| 6,080,183 A | 6/2000 | Tsugita et al. |
| 6,083,239 A | 7/2000 | Addis |
| 6,096,053 A | 8/2000 | Bates |
| 6,110,243 A | 8/2000 | Wnenchak et al. |
| 6,124,523 A | 9/2000 | Banas et al. |
| 6,132,438 A | 10/2000 | Fleischman et al. |
| 6,135,991 A | 10/2000 | Muni et al. |
| 6,136,016 A | 10/2000 | Barbut et al. |
| 6,139,527 A | 10/2000 | Laufer et al. |
| 6,139,573 A | 10/2000 | Sogard et al. |
| 6,152,144 A | 11/2000 | Lesh et al. |
| 6,156,055 A | 12/2000 | Ravenscroft |
| 6,161,543 A | 12/2000 | Cox et al. |
| 6,171,329 B1 | 1/2001 | Shaw et al. |
| 6,179,859 B1 | 1/2001 | Bates et al. |
| 6,214,029 B1 | 4/2001 | Thill et al. |
| 6,231,561 B1 | 5/2001 | Frazier et al. |
| 6,231,589 B1 | 5/2001 | Wessman et al. |
| 6,251,122 B1 | 6/2001 | Tsukernik |
| 6,258,115 B1 | 7/2001 | Dubrul |
| 6,270,490 B1 | 8/2001 | Hahnen |
| 6,277,138 B1 | 8/2001 | Levinson et al. |
| 6,290,674 B1 | 9/2001 | Roue et al. |
| 6,319,251 B1 | 11/2001 | Tu et al. |
| 6,328,727 B1 | 12/2001 | Frazier et al. |
| 6,342,062 B1 | 1/2002 | Suon et al. |
| 6,346,116 B1 | 2/2002 | Brooks et al. |
| 6,364,895 B1 | 4/2002 | Greenhalgh |
| 6,368,338 B1 | 4/2002 | Konya et al. |
| 6,371,971 B1 | 4/2002 | Tsugita et al. |
| 6,375,670 B1 | 4/2002 | Greenhalgh |
| 6,391,044 B1 | 5/2002 | Yadav et al. |
| 6,402,746 B1 | 6/2002 | Whayne et al. |
| 6,419,669 B1 | 7/2002 | Frazier et al. |
| 6,440,152 B1 | 8/2002 | Gainor et al. |
| 6,443,972 B1 | 9/2002 | Bosma et al. |
| 6,447,530 B1 | 9/2002 | Ostrovsky et al. |
| 6,468,291 B2 | 10/2002 | Bates et al. |
| 6,511,496 B1 | 1/2003 | Huter et al. |
| 6,517,573 B1 | 2/2003 | Pollock et al. |
| 6,547,760 B1 | 4/2003 | Samson et al. |
| 6,551,303 B1 | 4/2003 | Van Tassel et al. |
| 6,551,344 B2 | 4/2003 | Thill |
| 6,558,405 B1 | 5/2003 | McInnes |
| 6,562,058 B2 | 5/2003 | Seguin et al. |
| 6,599,308 B2 | 7/2003 | Amplatz |
| 6,652,555 B1 | 11/2003 | VanTassel et al. |
| 6,652,556 B1 | 11/2003 | VanTassel et al. |
| 6,689,150 B1 | 2/2004 | VanTassel et al. |
| 6,730,108 B2 | 5/2004 | Van Tassel et al. |
| 6,837,901 B2 | 1/2005 | Rabkin et al. |
| 6,855,153 B2 | 2/2005 | Saadat |
| 6,949,113 B2 | 9/2005 | Van Tassel et al. |
| 6,994,092 B2 | 2/2006 | van der Burg et al. |
| 7,011,671 B2 | 3/2006 | Welch |
| 7,044,134 B2 | 5/2006 | Khairkhahan et al. |
| 7,128,073 B1 | 10/2006 | van der Burg et al. |
| 8,062,282 B2 | 11/2011 | Kolb |
| 8,491,623 B2 | 7/2013 | Vogel et al. |
| 9,314,584 B1 | 4/2016 | Riley et al. |
| 10,758,241 B1 | 9/2020 | Lashinski et al. |
| 2001/0034537 A1 | 10/2001 | Shaw et al. |
| 2002/0022860 A1 | 2/2002 | Borillo et al. |
| 2002/0035374 A1 | 3/2002 | Borillo et al. |
| 2002/0062133 A1 | 5/2002 | Gilson et al. |
| 2002/0082638 A1 | 6/2002 | Porter et al. |
| 2002/0138094 A1 | 9/2002 | Borillo et al. |
| 2002/0138097 A1 | 9/2002 | Ostrovsky et al. |
| 2003/0023266 A1 | 1/2003 | Borillo et al. |
| 2003/0057156 A1 | 3/2003 | Peterson et al. |
| 2003/0181942 A1 | 9/2003 | Sutton et al. |
| 2003/0220667 A1 | 11/2003 | van der Burg et al. |
| 2004/0098031 A1 | 5/2004 | van der Burg et al. |
| 2004/0215230 A1 | 10/2004 | Frazier et al. |
| 2005/0004652 A1 | 1/2005 | van der Burg et al. |
| 2005/0113861 A1 | 5/2005 | Corcoran et al. |
| 2005/0203568 A1 | 9/2005 | Burg et al. |
| 2007/0232992 A1 | 10/2007 | Kutsko et al. |
| 2008/0033241 A1 | 2/2008 | Peh et al. |
| 2012/0172731 A1 | 7/2012 | Smith |
| 2013/0110106 A1* | 5/2013 | Richardson ........ A61B 18/1492 606/41 |
| 2013/0165965 A1 | 6/2013 | Carlson et al. |
| 2013/0345574 A1 | 12/2013 | Davies et al. |
| 2014/0018841 A1 | 1/2014 | Peiffer et al. |
| 2014/0039536 A1 | 2/2014 | Cully et al. |
| 2014/0100596 A1 | 4/2014 | Rudman et al. |
| 2014/0180239 A1 | 6/2014 | Mittermeyer et al. |
| 2014/0188157 A1 | 7/2014 | Clark |
| 2014/0323887 A1 | 10/2014 | Anderson et al. |
| 2014/0336612 A1 | 11/2014 | Frydlewski et al. |
| 2014/0364941 A1 | 12/2014 | Edmiston et al. |
| 2015/0119724 A1 | 4/2015 | Weber et al. |
| 2015/0196300 A1 | 7/2015 | Tischler et al. |
| 2016/0106437 A1 | 4/2016 | Van Der Burg et al. |
| 2016/0287259 A1 | 10/2016 | Hanson et al. |
| 2016/0310148 A1 | 10/2016 | Allen |
| 2017/0172722 A1 | 6/2017 | Dillard et al. |
| 2018/0042719 A1 | 2/2018 | Chambers |
| 2018/0338824 A1 | 11/2018 | VanTassal et al. |
| 2019/0223883 A1 | 7/2019 | Anderson et al. |
| 2019/0374229 A1 | 12/2019 | Anderson et al. |
| 2020/0107836 A1 | 4/2020 | O'Halloran |
| 2020/0138446 A1 | 5/2020 | Jockenhoevel et al. |
| 2020/0383688 A1 | 12/2020 | Olson et al. |
| 2021/0045691 A1* | 2/2021 | Zou ........................ A61B 5/686 |

FOREIGN PATENT DOCUMENTS

| | | |
|---|---|---|
| WO | 9640356 A1 | 12/1996 |
| WO | 9721402 A1 | 6/1997 |
| WO | 9728749 A1 | 8/1997 |
| WO | 9802100 A1 | 1/1998 |
| WO | 9817187 A1 | 4/1998 |
| WO | 9823322 A1 | 6/1998 |
| WO | 9827868 A1 | 7/1998 |
| WO | 9907289 A1 | 2/1999 |
| WO | 9908607 A1 | 2/1999 |
| WO | 9930640 A1 | 6/1999 |
| WO | 9944510 A1 | 9/1999 |
| WO | 0016705 A1 | 3/2000 |
| WO | 0027292 A1 | 5/2000 |
| WO | 0067669 A1 | 11/2000 |
| WO | 0115629 A1 | 3/2001 |

(56) References Cited

FOREIGN PATENT DOCUMENTS

| | | |
|---|---|---|
| WO | 0121247 A1 | 3/2001 |
| WO | 0130266 A1 | 5/2001 |
| WO | 0130267 A1 | 5/2001 |
| WO | 0130268 A1 | 5/2001 |
| WO | 0215793 A1 | 2/2002 |
| WO | 0224106 A2 | 3/2002 |
| WO | 03032818 A2 | 4/2003 |
| WO | 2015164836 A1 | 10/2015 |
| WO | 2016183495 A2 | 11/2016 |
| WO | 2018017935 A1 | 1/2018 |
| WO | 2018187732 A1 | 10/2018 |

OTHER PUBLICATIONS

PCT Search Report from co-pending Application PCT/US02/33808 dated May 20, 2003.

PCT Search Report from PCT/US99/26325 dated Feb. 15, 2000.

Cragg et al; "Nonsurgical Placement of Arterial Endoprosthesis: A New Technique Using Nitinol Wire," Radiology vol. 147, No. 1 pp. 261-263, Apr. 1983.

Cragg et al; "A New Percutaneous Vena Cava Filter", ALJ, 141: 601-604, Sep. 1983.

Sugita et al; "Nonsurgical Implantation of a Vascular Ring Prosthesis Using Thermal Shape Memory Ti/Ni Alloy (Nitinol Wire)," Trans. Am. Soc. Artif. Intern. Organs, vol. XXXII, 30-34, 1986.

Ruttenberg, Nonsurgical Therapy of Cardiac Disorders, Pediatric Consult, vol. 5, No. 2, pages not numbered, 1986.

Rashkind et al; "Nonsurgical Closure of Patent Ductus Arteriosus: Clinical Application of the Rashkind PDA Occluder System," Circulation 75, No. 3, 583-592-1987.

Lock et al; "Transcatheter Umbrella Closure of Congenital Heart Defects," Circulation, vol. 75, No. 3, 593-599, 1987.

Lock et al; "Transcatheter Closure of Artrial Septal Defects," Circulation, vol. 79, No. 5 1091-1099, May 1989.

Wessel et al; "Outpatient Closure of the Patent Ductus Arteriosus," Circulation, vol. 77, No. 5 1068-1071, 1988.

Invitation to Pay Additional Fees dated Feb. 22, 2019 for International Application No. PCT/US2018/066163.

Invitation to Pay Additional Fees dated Aug. 19, 2019 for International Application No. PCT/US2019/036063.

International Search Report and Written Opinion for Application No. PCT/US2019/030220, 11 pages, dated Aug. 2, 2019.

International Search Report and Written Opinion dated Sep. 9, 2019 for International Application No. PCT/US2019/033698.

\* cited by examiner

OCCLUSIVE MEDICAL DEVICE HAVING SENSING CAPABILITIES

CROSS-REFERENCE TO RELATED APPLICATIONS

This application claims the benefit of priority of U.S. Provisional Application No. 63/127,573 filed Dec. 18, 2020, the entire disclosure of which is hereby incorporated by reference.

BACKGROUND

The left atrial appendage (LAA) is a small organ attached to the left atrium of the heart as a pouch-like extension. In patients suffering from atrial fibrillation, the left atrial appendage may not properly contract with the left atrium, causing stagnant blood to pool within its interior, which can lead to the undesirable formation of thrombi within the left atrial appendage. Thrombi forming in the left atrial appendage may break loose from this area and enter the blood stream. Thrombi that migrate through the blood vessels may eventually plug a smaller vessel downstream and thereby contribute to stroke or heart attack. Clinical studies have shown that the majority of blood clots in patients with atrial fibrillation are found in the left atrial appendage. As a treatment, medical devices have been developed which are positioned in the left atrial appendage and deployed to close off the ostium of the left atrial appendage. Over time, the exposed surface(s) spanning the ostium of the left atrial appendage becomes covered with tissue (a process called endothelization), effectively removing the left atrial appendage from the circulatory system and reducing or eliminating the number of thrombi which may enter the blood stream from the left atrial appendage. A continuing need exists for improved medical devices and methods to monitor and control thrombus formation within the left atrial appendage of patients suffering from atrial fibrillation.

SUMMARY

An example occlusive implant includes an expandable framework configured to shift between a collapsed configuration and an expanded configuration, an occlusive member disposed along at least a portion of the expandable framework and a first collar attached to the expandable framework. The occlusive implant also includes a sensor housing coupled to the first collar, the sensor housing having a first end and a second end opposite the first end and a second collar slidably disposed along an outer surface of the sensor housing. Further, the second collar is coupled to the expandable framework via a spring. The occlusive implant also includes a sensor disposed along the second end of the sensor housing.

In addition or alternatively, wherein elongation of the spring is configured to shift the second collar from a first position in which the second collar is adjacent the first collar to a second position in which the second collar is adjacent the sensor.

In addition or alternatively wherein the spring is wrapped around the outer surface of the sensor housing.

In addition or alternatively, wherein the spring includes a first end coupled to the first collar and a second end coupled to the second collar.

In addition or alternatively, wherein the spring includes a first end coupled to the sensor housing and a second end coupled to the second collar.

In addition or alternatively, wherein the first collar includes an aperture, and wherein the sensor housing extends within the aperture of the first collar.

In addition or alternatively, wherein the first collar extends circumferentially around an outer surface of the sensor housing.

In addition or alternatively, wherein the first collar and the expandable framework are formed from a monolithic sheet of material.

In addition or alternatively, wherein the expandable framework further includes a plurality of struts attached to the first collar.

In addition or alternatively, wherein the expandable framework further includes a plurality of struts attached to the sensor housing.

In addition or alternatively, wherein the first collar is configured to remain stationary relative to the sensor housing while the expandable framework shifts between the collapsed configuration and the expanded configuration.

In addition or alternatively, wherein the first collar is configured to remain stationary relative to the sensor housing while the second collar shifts along the outer surface of the sensor housing.

In addition or alternatively, wherein the sensor is positioned within the expandable framework such that the sensor faces away from the occlusive member.

In addition or alternatively, wherein a first portion of the occlusive member is attached to the expandable framework and a second portion of the occlusive member is attached to the second collar.

Another example occlusive implant includes an expandable framework configured to shift between a collapsed configuration and an expanded configuration, the expandable framework including a plurality of struts spaced around a longitudinal axis of the expandable framework. The occlusive implant also includes an occlusive member disposed along at least a portion of the expandable framework and a first collar attached to the plurality of struts of the expandable framework, the first collar defining an aperture, where a central region of the aperture is aligned with the longitudinal axis of the expandable framework. The occlusive collar also includes a sensor housing coupled to the first collar and extending along the longitudinal axis of the expandable framework, the sensor housing having a first end and a second end opposite the first end. The occlusive implant also includes a second collar slidably disposed along an outer surface of the sensor housing, wherein the second collar is coupled to the expandable framework via a spring. Further, the occlusive implant includes a sensor disposed along the second end of the sensor housing.

In addition or alternatively, wherein elongation of the spring is configured to shift the second collar from a first position in which the second collar is adjacent the first collar to a second position in which the second collar is adjacent the sensor.

In addition or alternatively, wherein the spring is wrapped around the outer surface of the sensor housing.

In addition or alternatively, wherein the spring includes a first end coupled to the first collar and a second end coupled to the second collar.

In addition or alternatively, wherein the first collar is configured to remain stationary relative to the sensor housing while the second collar shifts along the outer surface of the sensor housing.

An example method for occluding a left atrial appendage includes advancing an occlusive implant to the left atrial appendage, the occlusive implant including an expandable framework configured to shift between a collapsed configuration and an expanded configuration. The occlusive implant also includes an occlusive member disposed along at least a portion of the expandable framework and a first collar attached to the expandable framework. The occlusive implant also includes a sensor housing coupled to the first collar, the sensor housing having a first end and a second end opposite the first end. The occlusive implant also includes a second collar slidably disposed along an outer surface of the sensor housing, wherein the second collar is coupled to the expandable framework via a spring. The occlusive implant also includes a sensor disposed along the second end of the sensor housing. The method also includes expanding the expandable framework within the left atrial appendage.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
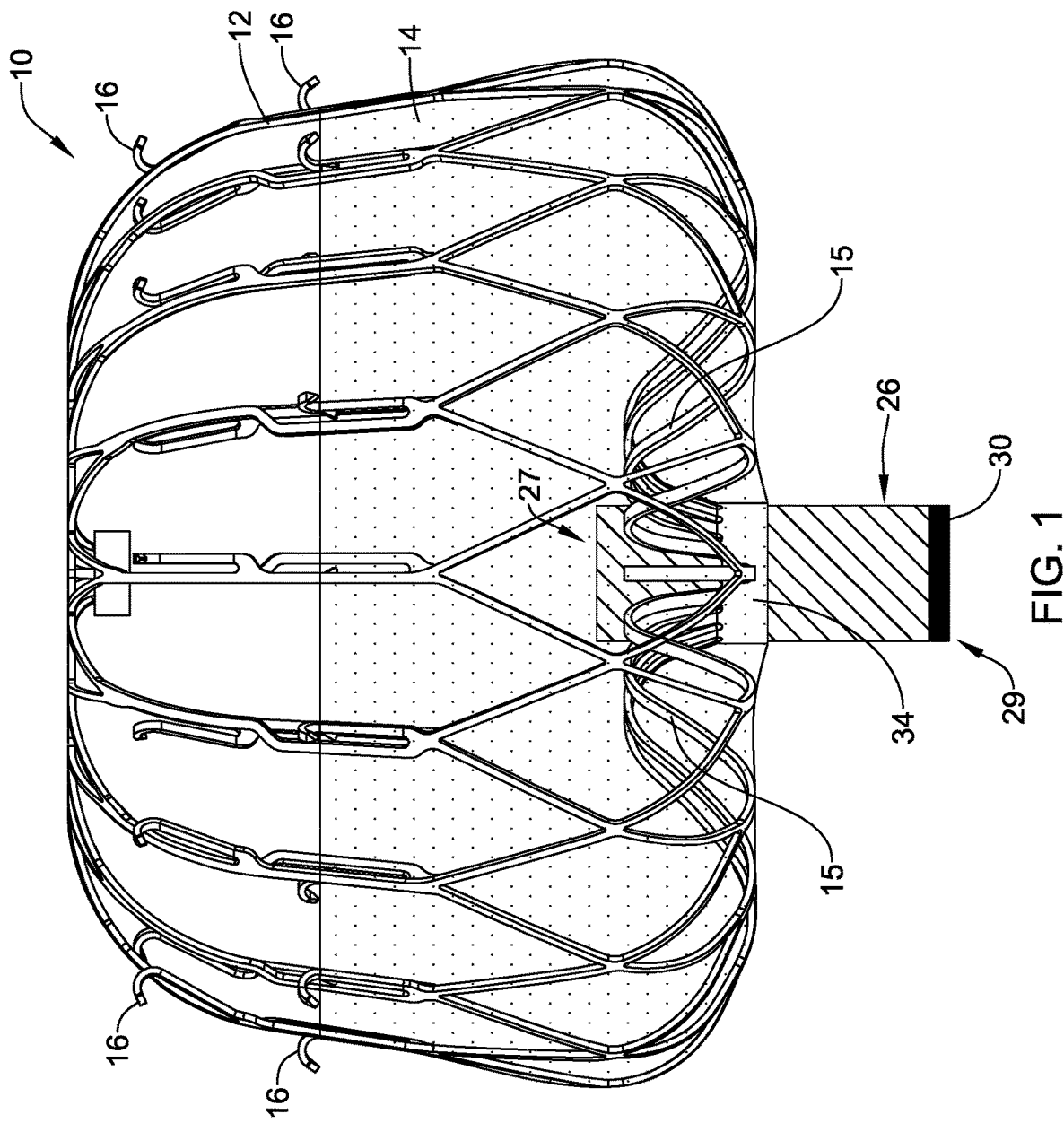
FIG. 1 is a plan view of an example occlusive implant.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed disclosure. Those skilled in the art will recognize that the various elements described and/or shown may be arranged in various combinations and configurations without departing from the scope of the disclosure. The detailed description and drawings illustrate example embodiments of the claimed disclosure. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified. The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The occurrence of thrombi in the left atrial appendage (LAA) during atrial fibrillation may be due to stagnancy of blood pooling in the LAA. The pooled blood may still be pulled out of the left atrium by the left ventricle, however less effectively due to the irregular contraction of the left atrium caused by atrial fibrillation. Therefore, instead of an active support of the blood flow by a contracting left atrium and left atrial appendage, filling of the left ventricle may depend primarily or solely on the suction effect created by the left ventricle. However, the contraction of the left atrial appendage may not be in sync with the cycle of the left ventricle. For example, contraction of the left atrial appendage may be out of phase up to 180 degrees with the left ventricle, which may create significant resistance to the desired flow of blood. Further still, most left atrial appendage geometries are complex and highly variable, with large irregular surface areas and a narrow ostium or opening compared to the depth of the left atrial appendage. These aspects as well as others, taken individually or in various combinations, may lead to high flow resistance of blood out of the left atrial appendage.

In an effort to reduce the occurrence of thrombi formation within the left atrial appendage and prevent thrombi from entering the blood stream from within the left atrial appendage, it may be desirable to develop medical devices and/or occlusive implants that close off the left atrial appendage from the heart and/or circulatory system, thereby lowering the risk of stroke due to thrombolytic material entering the blood stream from the left atrial appendage. Additionally, in some instances it may be desirable to develop medical devices and/or occlusive implants that provide diagnostic functionality to the implantable medical device. For example, it may be desirable to design the medical device to include a sensor which may sense a variety of diagnostic information such as left atrial pressure, temperature, oxygen levels or the like. Example medical devices and/or occlusive implants designed to seal the left atrial appendage (or other similar openings) while also having diagnostic sensing capabilities are disclosed herein.

FIG. 1 illustrates an example occlusive implant 10. The occlusive implant 10 may include an expandable framework 12. The occlusive implant 10 may also include an occlusive member 14 disposed on, disposed over, disposed about, or covering at least a portion of the expandable framework 12. In some embodiments, the occlusive member 14 may be disposed on, disposed over, disposed about or cover at least a portion of an outer (or outwardly-facing) surface of the expandable framework 12. FIG. 1 further illustrates that the occlusive member 14 may extend only partially along the longitudinal extent (e.g., longitudinal axis) of the expandable framework 12. However, this is not intended to be limiting. Rather, the occlusive member 14 may extend along the longitudinal extent of the expandable framework to any degree (e.g., the full longitudinal extend of the expandable framework 12).

In some embodiments, the occlusive member 14 may be permeable or impermeable to blood and/or other fluids, such as water. In some embodiments, the occlusive member 14 may include a woven, braided and/or knitted material, a fiber, a sheet-like material, a fabric, a polymeric membrane, a metallic or polymeric mesh, a porous filter-like material, or other suitable construction. In some embodiments, the occlusive member 14 may prevent thrombi (i.e. blood clots, etc.) from passing through the occlusive member 14 and out of the left atrial appendage into the blood stream. In some embodiments, the occlusive member 14 may promote endothelialization after implantation, thereby effectively removing the left atrial appendage from the patient's circulatory system. Some suitable, but non-limiting, examples of materials for the occlusive member 14 are discussed below.

FIG. 1 further illustrates that the expandable framework 12 may include a plurality of anchor members 16 disposed about a periphery of the expandable framework 12. The plurality of anchor members 16 may extend radially outward from the expandable framework 12. In some embodiments, at least some of the plurality of anchor members 16 may each have and/or include a body portion and a tip portion projecting circumferentially therefrom, as shown in FIG. 1. Some suitable, but non-limiting, examples of materials for the expandable framework 12 and/or the plurality of anchor members 16 are discussed below.

In some examples, the expandable framework 12, the plurality of anchor members 16 and/or other members/components of the expandable framework 12 disclosed herein may be integrally formed and/or cut from a unitary (e.g., monolithic) member. In some embodiments, the expandable framework 12 and the plurality of anchor members 16 may be integrally formed and/or cut from a unitary tubular member and subsequently formed and/or heat set to a desired shape in the expanded configuration. In some embodiments, the expandable framework 12 and the plurality of anchor members 16 may be integrally formed and/or cut from a unitary flat member, and then rolled or formed into a tubular structure and subsequently formed and/or heat set to the desired shape in the expanded configuration. Some exemplary means and/or methods of making and/or forming the expandable framework 12 include laser cutting, machining, punching, stamping, electro discharge machining (EDM), chemical dissolution, etc. Other means and/or methods are also contemplated.

As illustrated in FIG. 1, the plurality of anchor members 16 disposed along the expandable framework 12 may include two rows of anchor members 16. However, this is not intended to be limiting. Rather, the expandable framework 12 may include a single row of anchor members 16. In other examples, the expandable framework 12 may include more than two rows of anchor members 16. For example, in some instances the expandable framework 12 may include 1, 2, 3, 4 or more rows of anchor members 16.

FIG. 1 further illustrates that the occlusive implant 10 may include a sensor housing 26 coupled to the framework 12. The sensor housing 26 may include a first end 27 and a second end 29 opposite the first end 27. As illustrated in FIG. 1, the frame 12 may include one or more struts 15 which are fixedly attached (e.g., welding, glued, soldered, crimped, etc.) to a cylindrical collar 34 (e.g., cylindrical band, cylindrical ring) which is designed to be positioned circumferentially around the outer surface of the sensor housing 26. The collar 34 may include an aperture, the center of which may be generally aligned with the longitudinal axis of the expandable framework 12. However, while the occlusive implant 10 illustrated in FIG. 1 shows the struts 15 welded to the collar 34, it is contemplate that, in other examples, the struts 15 may be directly welded to the sensor housing 26.

In some examples, the collar 34 may include a cylindrical metallic ring (e.g., a metallic collar) which is designed to permit the sensor housing 26 to extend therethrough. In some examples, the collar 34 may be fully or partially embedded in the sensor housing 26. For example, the sensor housing 26 may be over-molded over top of the collar 34. However, it is contemplated that the collar 34 may be fixedly attached to the sensor housing 26 via a variety of different attachment techniques. For example, the collar 34 may be attached to the sensor housing 26 using one or more of a screw thread, bayonet attachment, crimping, welding, press fitting, c-clips, a retaining ring, a snap fit, adhesives, gluing, soldering or any other suitable attachment technique.

The collar 34 may be constructed of a variety of materials. For example, the collar 34 may be formed from a metal, metal alloy, a polymer, a ceramic or any combinations thereof. Further, in some instances, the collar 34 may be constructed from the same material as the frame 12. For example, the frame 12 (including the struts 15) and the collar and 34 may be a monolithic structure whereby the frame 12, struts 15 and the collar 34 may be formed from the same monolithic base material. However, it can be appreciated that, in some examples, the frame 12 and the collar 34 may constructed as separate components, whereby the struts 15 of the frame 12 may be affixed to the collar 34. FIG. 1 illustrates that the struts 15 may be affixed around the outer surface of the collar 34, extending along the entire outer circumference of the collar 34. In other words, the struts 15 may be attached to the band at evenly (or unevenly) spaced intervals extending 360 degrees around the outer circumference of the collar 34.

A discussed above, the collar 34 may be designed to include a centralized aperture (e.g., opening) designed to permit the sensor housing 26 to extend therethrough. It can be appreciated that the centralized aperture of the collar 34 may include an inner diameter. It can be further appreciated that the sensor housing 26 may include an outer diameter which is sized to fit within the inner diameter of the collar 34. FIG. 1 illustrates that the first end 27 of the sensor housing 26 may be aligned such that, when the occlusive implant 10 is positioned in the ostium of left atrial appendage, the first end 27 of the sensor housing 26 is oriented toward (e.g., pointing into) the left atrial appendage. Additionally, FIG. 1 illustrates that the second end 29 of the sensor housing 26 may be aligned such that, when the occlusive implant 10 is positioned in the ostium of left atrial appendage, the second end 29 of the sensor housing 26 may point toward the left atrium of the heart. The orientation of the sensor housing 26 as the occlusive implant 10 is positioned within the ostium of the left atrial appendage will be described in greater detail below with respect to FIG. 2.

FIG. 1 further illustrates that the sensor housing 26 may include a sensor 30 disposed along the second end 29 of the sensor housing 26. The sensor 30 may include a variety of different sensors. For example, the sensor 30 may include a pressure sensor, a temperature sensor, an oxygen sensor, an electrical sensor (e.g., an EKG sensor), an impedance sensor, or the like. Further, sensors contemplated herein may be configured to sense heart rhythms, blood chemical tests (e.g., a NT-proBNP test), or other similar tests. Additionally, it can be appreciated that the sensor 30 (and components defining the sensor 30) may be integrated into the sensor housing 26. For example, in some instances the sensor 30 (and components thereof) may be fixedly attached to the second end 29 of the sensor housing. In some examples, the sensor 30 may be fully or partially embedded into the material used to construct the sensor housing 26.

It can be appreciated that, in some examples, the collar 34 may include one or more fixation components designed to allow the occlusive member 14 to attach thereto. For example, the collar 34 may include hooks, holes, tines, etc. designed to allow the occlusive member 14 to attach thereto. A discussed above, in some examples, the occlusive member 14 may constructed from a fabric, and therefore, may able to hook onto one or more of the hooks, holes, tines, etc. located on the collar 34.

The sensor housing 26 may be formed from a variety of materials. For example, the sensor housing may be formed from a glass, acrylic, polymer, metal, metal alloy, a ceramic or any combinations thereof. Additionally, the sensor housing 26 (including the sensor 30) may be formed from a biocompatible material.

Figure 2:
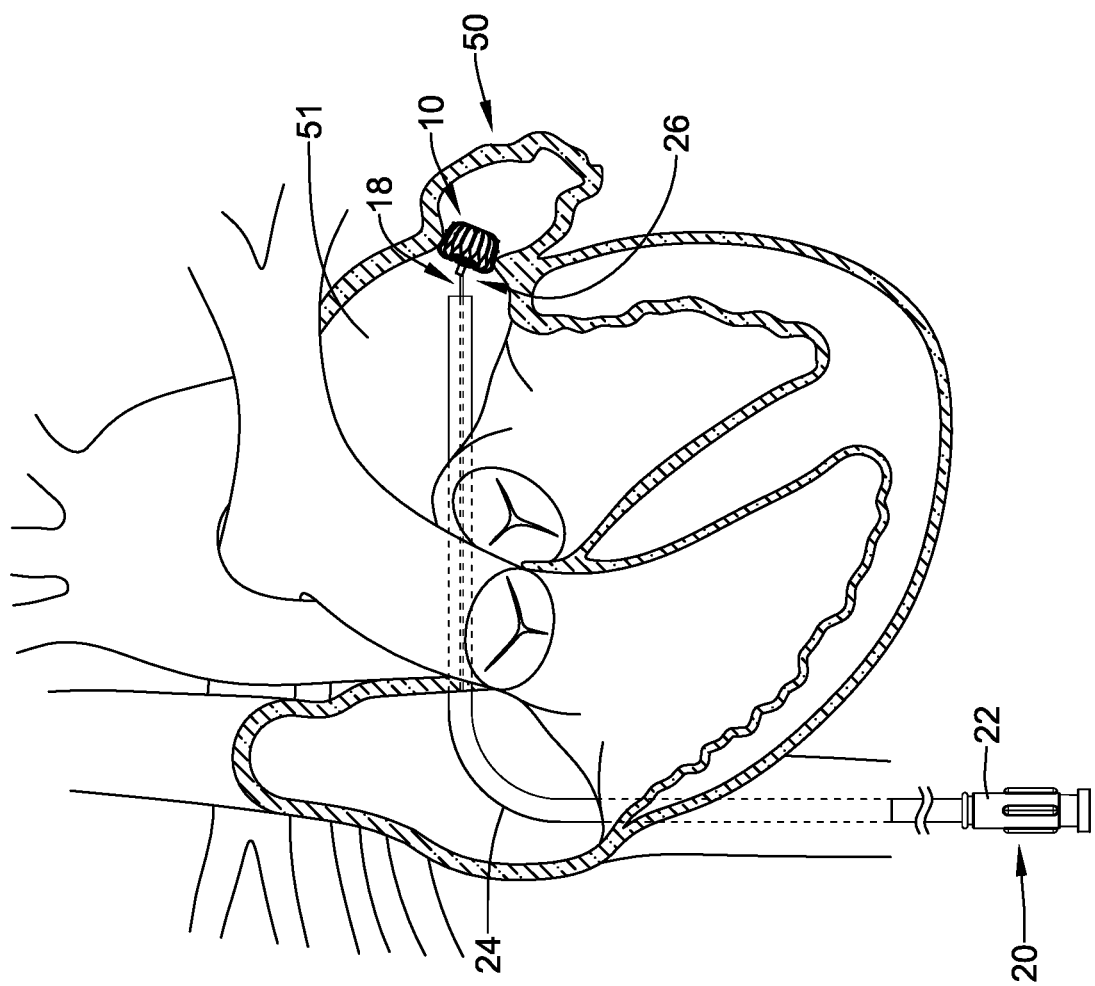
FIG. 2 illustrates an example occlusive implant positioned in the heart.

FIG. 2 illustrates that the occlusive implant 10 may be inserted and advanced through a body lumen via an occlusive implant delivery system 20. FIG. 2 further illustrates the occlusive implant 10 being delivered and positioned within the left atrial appendage 50. In some instances, an occlusive implant delivery system 20 may include a delivery catheter 24 which is guided toward the left atrium 51 via various chambers and lumens of the heart (e.g., the inferior vena cava, the right atrium, etc.) to a position adjacent the left atrial appendage 50.

The delivery system 20 may include a hub member 22 coupled to a proximal region of the delivery catheter 24. The hub member 22 may be manipulated by a clinician to direct the distal end region of the delivery catheter 24 to a position adjacent the left atrial appendage 50. In some embodiments, an occlusive implant delivery system may include a core wire 18. Further, a proximal end of the expandable framework 12 may be configured to releasably attach, join, couple, engage, or otherwise connect to the distal end of the core wire 18. In some embodiments, an end region of the expandable framework 12 may include a threaded insert coupled thereto. In some embodiments, the threaded insert may be configured to and/or adapted to couple with, join to, mate with, or otherwise engage a threaded member disposed at the distal end of a core wire 18. Other means of releasably coupling and/or engaging the proximal end of the expandable framework 12 to the distal end of the core wire 18 are also contemplated.

It can be appreciated that, in some instances, the core wire 18 (or any other component of the delivery system 20) may be releasably attached to the sensor housing 26. For example, in some instances, the core wire 18 may be releasably attached, engaged, joined, coupled, or otherwise connected to the sensor housing 26, the expandable framework 12, or any other component of the medical device 10 via a variety of different connection methods. For example, it is contemplated that the sensor housing 26 may include a threaded component configured to and/or adapted to couple with, join to, mate with, or otherwise engage a threaded member disposed at the distal end of a core wire 18.

Figure 3:
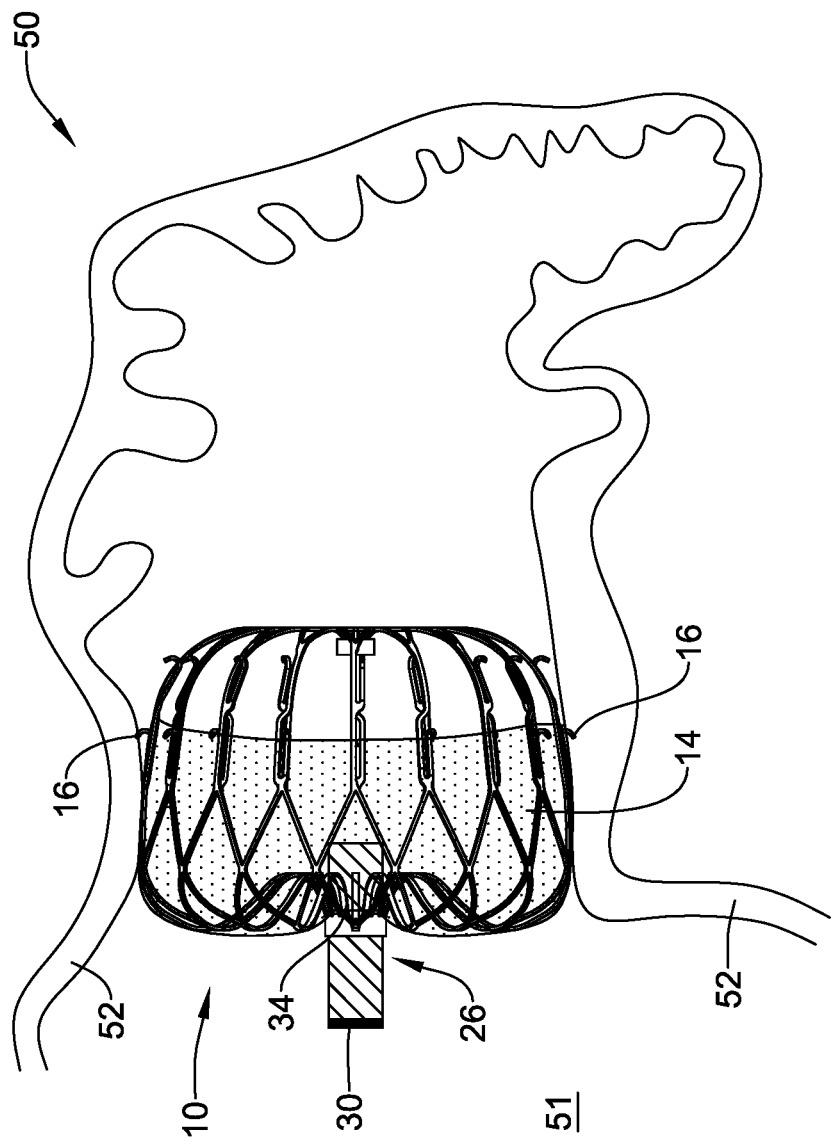
FIG. 3 illustrates an example occlusive implant positioned in the left atrial appendage.

FIG. 3 illustrates the occlusive implant 10 positioned within the left atrial appendage 50 via the delivery catheter 24 (described above with respect to FIG. 2). As discussed above, in some examples, the implant 10 may be configured to shift between a collapsed configuration and an expanded configuration. For example, in some instances, the occlusive implant 10 may be in a collapsed configuration during delivery via an occlusion implant delivery system, whereby the occlusive implant 10 expands to an expanded configuration once deployed from the occlusion implant delivery system.

Additionally, FIG. 3 illustrates that the expandable framework 12 may be compliant and, therefore, substantially conform to and/or be in sealing engagement with the shape and/or geometry of a lateral wall of a left atrial appendage 50 in the expanded configuration. In some embodiments, the occlusive implant 10 may expand to a size, extent, or shape less than or different from a maximum unconstrained extent, as determined by the surrounding tissue 52 and/or lateral wall of the left atrial appendage. Additionally, FIG. 3 illustrates that the expandable framework 12 may be held fixed adjacent to the left atrial appendage by one or more anchoring members 16.

Further, it can be appreciated that the elements of the expandable framework 12 may be tailored to increase the flexibility and compliance of the expandable framework 12 and/or the occlusive implant 10, thereby permitting the expandable framework 12 and/or the occlusive implant 10 to conform to the tissue around it, rather than forcing the tissue to conform to the expandable framework 12 and/or the occlusive implant 10. Additionally, in some instances, it may be desirable to design the occlusive implant 10 discussed above to include various features, components and/or configurations which improve the sealing capabilities of the occlusive implant 10 within the left atrial appendage. Several example occlusion devices including various sealing features are disclosed below.

As described above, FIG. 3 further illustrates the position of the sensor housing 26 (including the sensor 30) relative to the left atrial appendage 50 and the left atrium 51. For example, FIG. 3 illustrates that the sensor housing 26 may be attached to the collar 34 such that the sensor 30 points toward and extends into the left atrium 51. Positioning the sensor housing 26 such that the sensor 30 points toward extends into the left atrium 51 may permit the sensor 30 to sense diagnostic parameters (e.g., pressure, temperature, oxygen levels, etc.) of the left atrium and/or the left atrial appendage. Positioning the sensor 30 adjacent to the second end 29 of the sensor housing 26 permits the sensor 30 be in direct communication with the left atrium.

Figure 4:
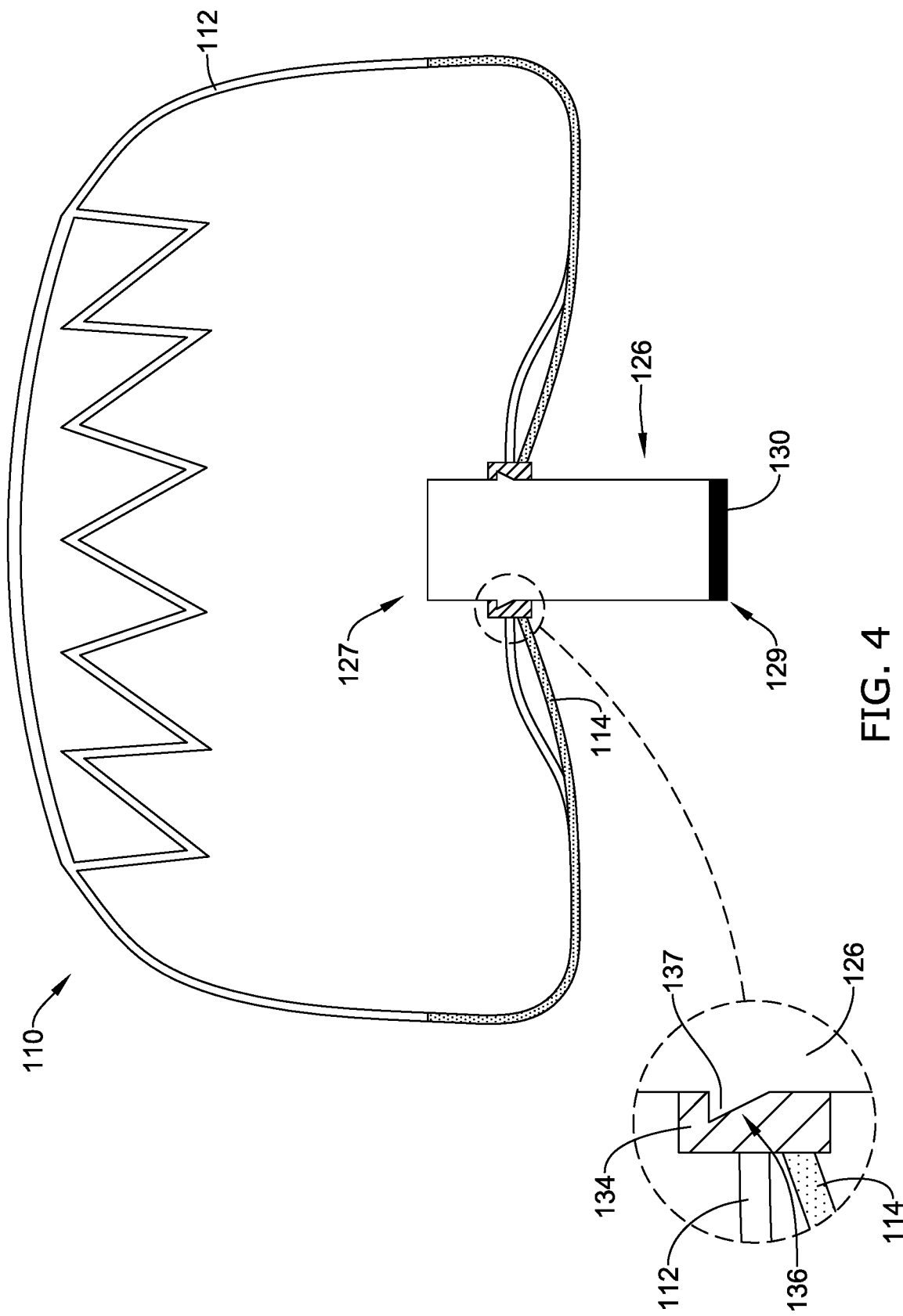
FIG. 4 is a plan view of another example occlusive implant.

FIG. 4 illustrates another medical device 110, which may be similar in form and function to the occlusive implant 10 discussed above. For example, the medical device 110 may include an expandable framework 112 and an occlusive member 114 disposed on, disposed over, disposed about, or covering at least a portion of the expandable framework 112. The expandable framework 112 and the occlusive member 114 may be similar in form and function to the expandable framework 12 and the occlusive member 14 described above. Additionally, in the interest of simplicity, FIG. 4 illustrates a "silhouette" of the occlusive implant 110 in an expanded configuration. It can be appreciated that the expandable framework 112 may be configured to shift between an unexpanded configuration and an expanded configuration.

FIG. 4 illustrates that the medical device 110 may further include a sensor housing 126 coupled to a collar 134. The sensor housing 126 may include a first end 127 and a second end 129 opposite the first end 127. The sensor housing 126 may further include a sensor 130 disposed along the second end 129 of the sensor housing 126. The sensor 130 and the collar 134 may be similar in form and function to the sensor 30 described above. For example, the sensor 130 may include a variety of different types of sensors. For example, as discussed above, the sensor 130 may include a pressure sensor, a temperature sensor, an oxygen sensor, an electrical sensor (e.g., an EKG sensor), an impedance sensor, or the like. Additionally, it can be appreciated that the sensor 130 (and components defining the sensor 130) may be integrated into the sensor housing 126. In some instances, the sensor 130 (and components thereof) may be fixedly attached to the second end 129 of the sensor housing. For examples, the sensor 130 may be fully or partially embedded into the material used to construct the sensor housing 126.

The detailed view of FIG. 4 further illustrates that the sensor housing 126 may include one or more features which facilitate its attachment to the collar 134. For example, FIG. 4 illustrates that the sensor housing 126 may include one or more projections 137 extending radially away from an outer surface of the sensor housing 126. It can be appreciated that, in some examples, the projection 137 may be one or more individual projections extending radially away from the outer surface of the sensor housing 126. However, in other examples, the projection 137 may include a circumference lip (e.g., shelf, ramp, shoulder, rim, ridge, etc.) that extends radially away from the outer surface of the sensor housing 126 but also extends circumferentially around the outer surface of the sensor housing 126.

FIG. 4 further illustrates that the collar 134 may include a recess 136 designed to mate with the projection 137 of the sensor housing 126. In some examples, it can be appreciated that the projection 137 may engage (e.g., snap, crimp, press-fit, etc.) with the recess 136 such that the sensor housing 126 is fixedly attached to the collar 134. It can further be appreciated that while the FIG. 4 illustrates that the sensor housing 126 includes a projection 137 extending radially away from the outer surface of the sensor housing 126 and mating with a recess 136 in the collar 134, it is contemplated that the collar 134 may include a projection extending radially way from its surface whereby it mates with a recess located in the sensor housing 126.

The detailed view of FIG. 4 also illustrates the frame 112 may be fixedly attached to the collar 134. Additionally, detailed view of FIG. 4 also illustrates the occlusive member 114 may be fixedly attached to the collar 134. However, it is contemplated that the occlusive member 114, in some examples, may be fixedly attached to one or more portions of the frame 112 (and may or may not be directly attached to the collar 134).

Figure 5:
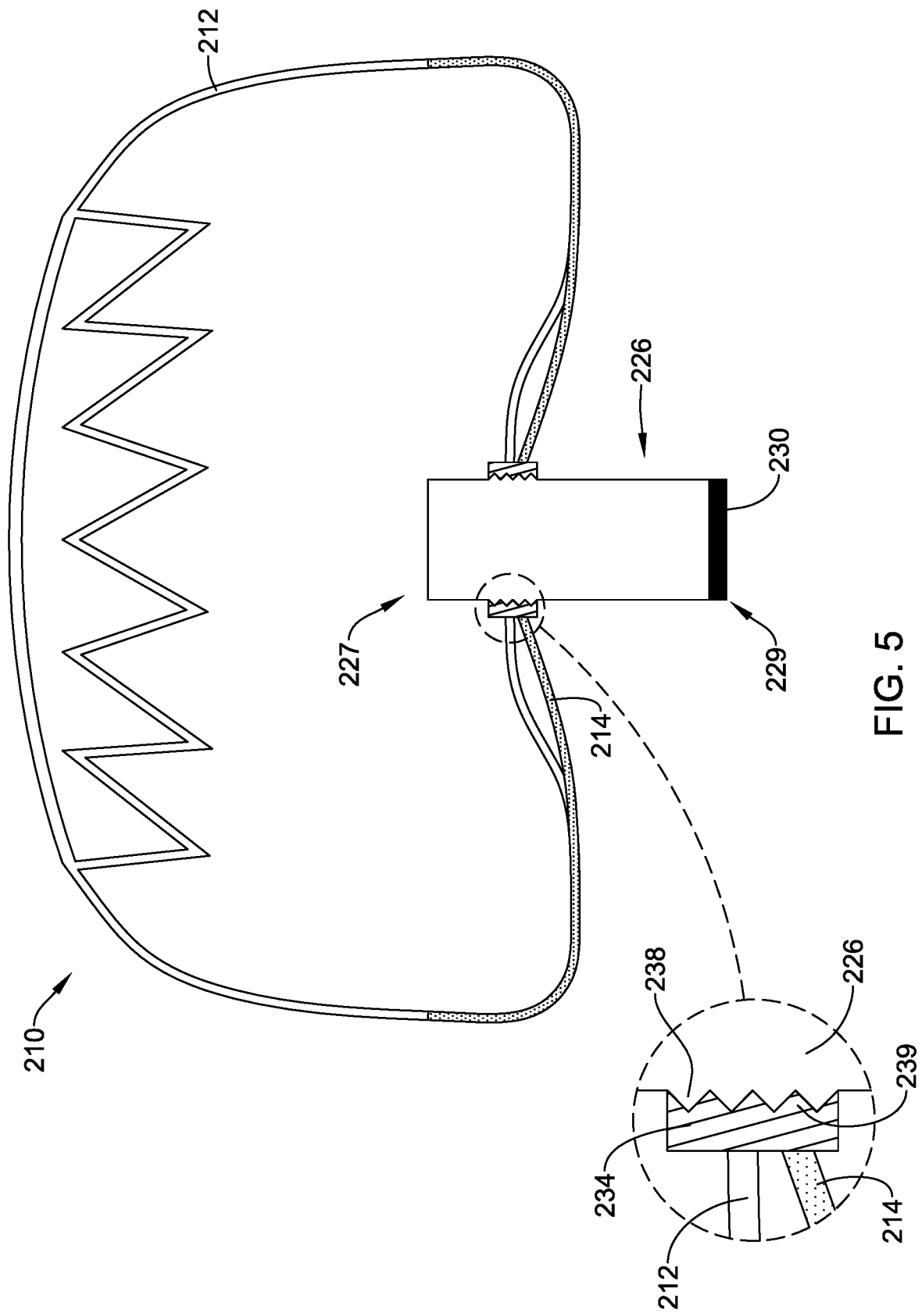
FIG. 5 is a plan view of another example occlusive implant.

FIG. 5 illustrates another medical device 210, which may be similar in form and function to the occlusive implants 10/110 discussed above. For example, the medical device 210 may include an expandable framework 212 and an occlusive member 214 disposed on, disposed over, disposed about, or covering at least a portion of the expandable framework 212. The expandable framework 212 and the occlusive member 214 may be similar in form and function to the expandable framework 12/112 and occlusive member 14/114 described above. Additionally, in the interest of simplicity, FIG. 5 illustrates a "silhouette" of the occlusive implant 210 in an expanded configuration. It can be appreciated that the expandable framework 212 may be configured to shift between an unexpanded configuration and an expanded configuration.

FIG. 5 illustrates that the medical device 210 may further include a sensor housing 226 coupled to a collar 234. The sensor housing 226 may include a first end 227 and a second end 229 opposite the first end 227. The sensor housing 226 may further include a sensor 230 disposed along the second end 229 of the sensor housing 226. The sensor 230 and the collar 234 may be similar in form and function to the sensor 30/130 described above. For example, the sensor 230 may include a variety of different types of sensors. For example, the sensor 230 may include a pressure sensor, a temperature sensor, an oxygen sensor, or the like. Additionally, it can be appreciated that the sensor 230 (and components defining the sensor 230) may be integrated into the sensor housing 226. In some instances, the sensor 230 (and components thereof) may be fixedly attached to the second end 229 of the sensor housing. For examples, the sensor 230 may be fully or partially embedded into the material used to construct the sensor housing 226.

The detailed view of FIG. 5 further illustrates that the sensor housing 226 may include one or more features which facilitate its attachment to the collar 234. For example, FIG. 5 illustrates that the sensor housing 226 may include a one or more threads 238 disposed along the outer surface of the sensor housing 226. FIG. 5 further illustrates that the collar 234 may include one or more threads 239 designed to engage and mate with the threads 238 disposed along the sensor housing 226, such engagement of the threads 238 of the sensor housing with the threads 239 of the collar 234 fixedly attach the sensor housing 226 to the collar 234.

The detailed view of FIG. 5 also illustrates the frame 212 may be fixedly attached to the collar 234. Additionally, detailed view of FIG. 5 also illustrates the occlusive member 214 may be fixedly attached to the collar 234. However, it is contemplated that the occlusive member 214, in some examples, may be fixedly attached to one or more portions of the frame 212 (and may or may not be directly attached to the collar 234).

Figure 6:
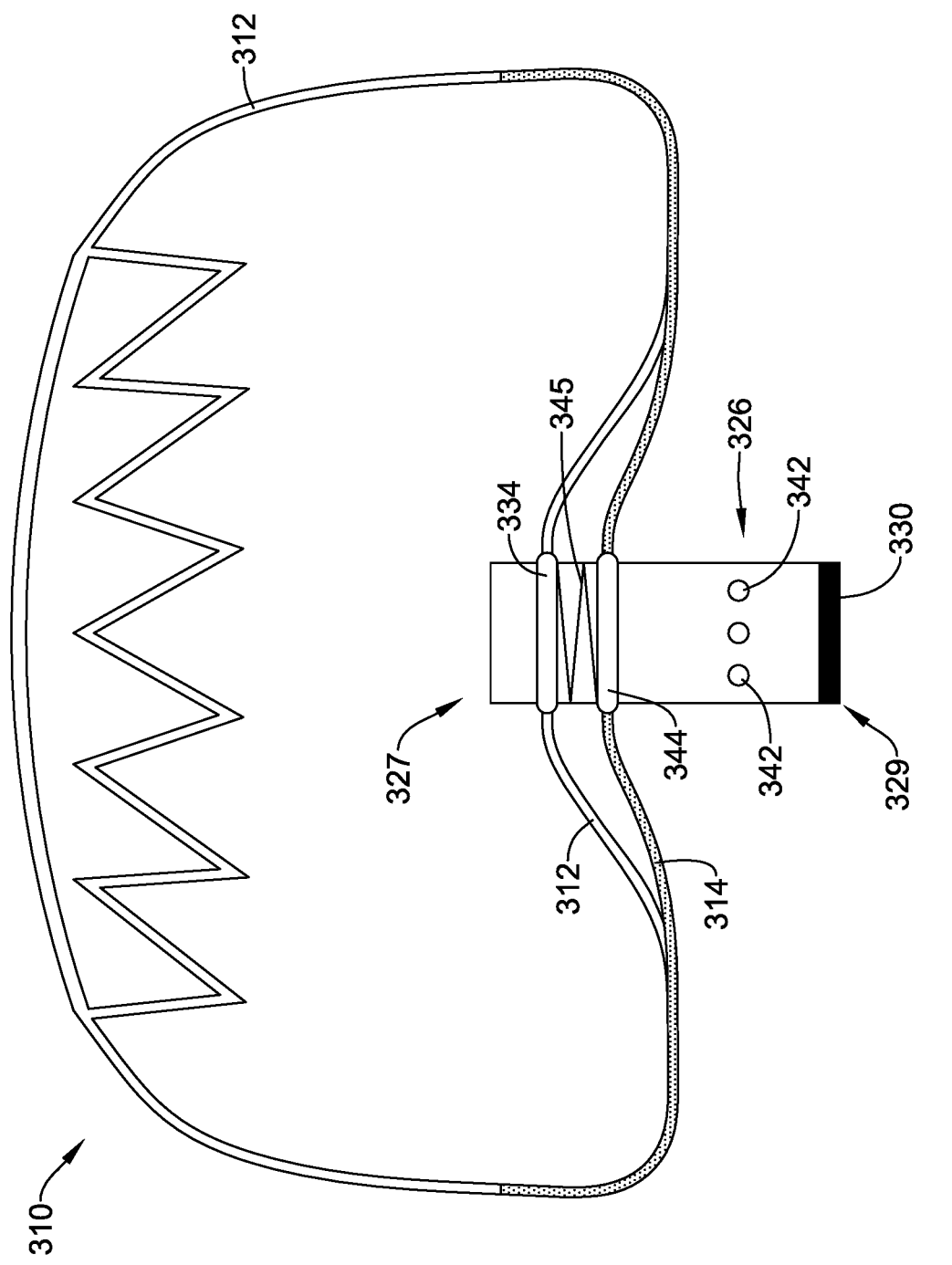
FIG. 6 is a plan view of another example occlusive implant.
Figure 7:
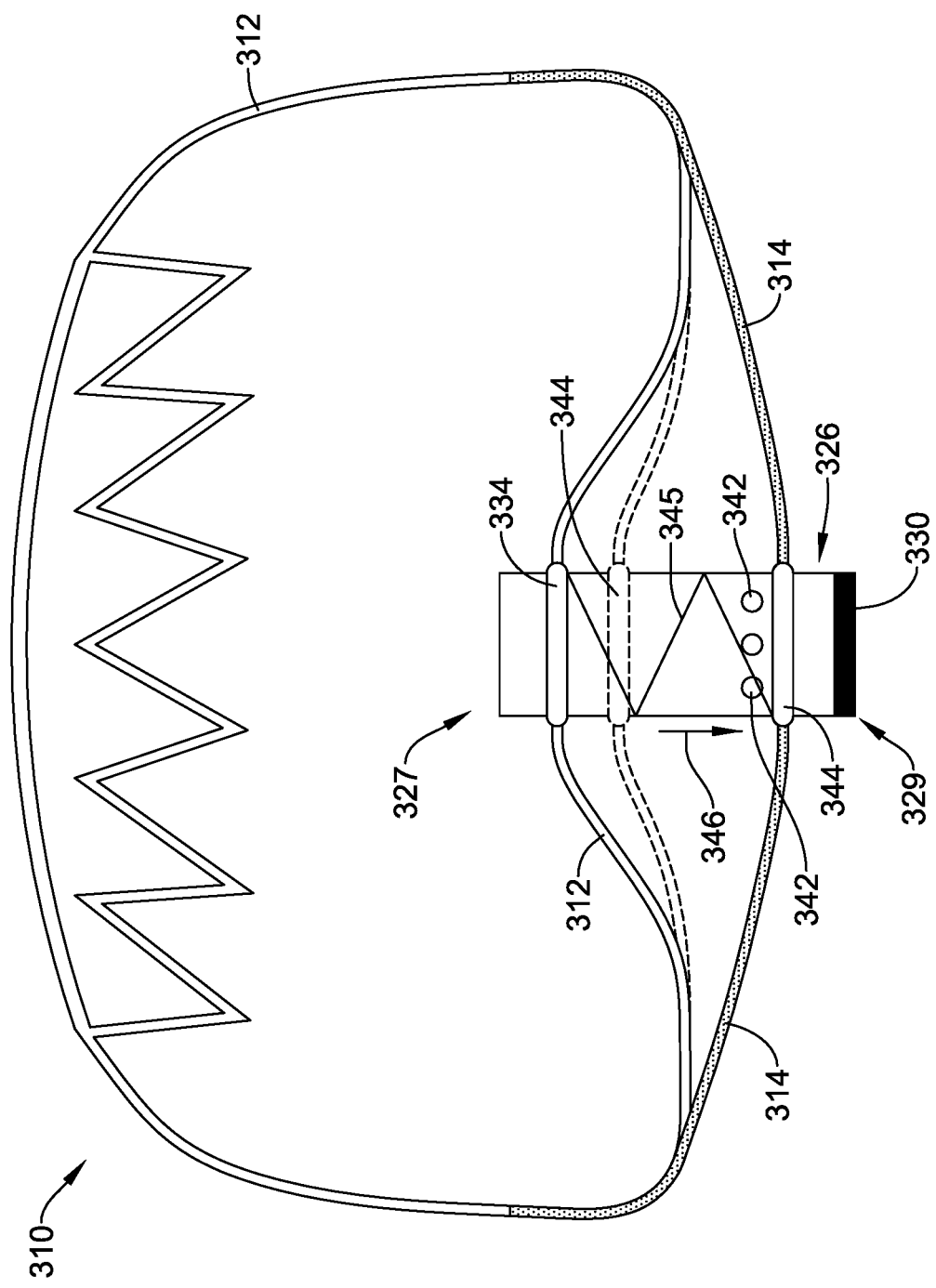
FIG. 7 is a plan view of another example occlusive implant.

FIGS. 6-7 illustrates another medical device 310, which may be similar in form and function to the occlusive implants discussed above. For example, the medical device 310 may include an expandable framework 312 and an occlusive member 314 disposed on, disposed over, disposed about, or covering at least a portion of the expandable framework 312. The expandable framework 312 and the occlusive member 314 may be similar in form and function to the expandable framework and occlusive members described above. Additionally, in the interest of simplicity, FIGS. 6-7 illustrates a "silhouette" of the occlusive implant 310 in an expanded configuration. It can be appreciated that the expandable framework 312 may be configured to shift between an unexpanded configuration and an expanded configuration.

FIGS. 6-7 further illustrate that the medical device 310 may further include a sensor housing 326 coupled to a first collar 334. The sensor housing 326 may include a first end 327 and a second end 329 opposite the first end 327. The sensor housing 326 may further include a sensor 330 disposed along the second end 329 of the sensor housing 326. The sensor 330 and the first collar 334 may be similar in form and function to other sensors described above. For example, the sensor 330 may include a variety of different types of sensors. For example, the sensor 330 may include a pressure sensor, a temperature sensor, an oxygen sensor, or the like. Additionally, it can be appreciated that the sensor 330 (and components defining the sensor 330) may be integrated into the sensor housing 326. In some instances, the sensor 330 (and components thereof) may be fixedly attached to the second end 329 of the sensor housing. For examples, the sensor 330 may be fully or partially embedded into the material used to construct the sensor housing 326.

FIG. 6 further illustrates that in some examples, the sensor housing 326 may include one or more attachment members 342 which may be designed to aid in the attachment of a medical device delivery system (not shown in FIG. 6, but an example is illustrated and described in FIG. 2). For example, FIG. 6 illustrates that the sensor housing 326 may include a plurality of apertures 342 which may be utilized in the attachment of a delivery system designed to deliver the occlusive member 310 shown in FIG. 6. It can further be appreciated that while FIG. 6 illustrates the attachment members 342 as a series of apertures, this is not intended to be limiting. Rather, it is contemplated that the sensor housing 326 may include a variety of different attachment members 342 designed engage an example occlusive member delivery system. For example, the attachment members 342 may include bumps, hooks, pins, threads, rip cord.

Additionally, while the sensor housing 326 has been described as including the attachment members 342, it is further contemplated that the attachment members 342 may be positioned and/or included on any portion of the expandable framework 312. For example, a core wire (not shown in FIG. 6, but illustrated in FIG. 2) may be attached to any component of the occlusive member 310 via an attachment member 342 positioned along any component of the occlusive member 310 including the sensor housing 326, the expandable framework 312 or both the sensor housing 326 and the expandable framework 312.

As shown in FIG. 6, the attachment members 342 may be positioned along the sensor housing 326 such that the attachment members 342 are spaced away from sensor 330. In other words, the attachment members 342 may be spaced toward the first end 327 of the sensor housing relative to the position of the sensor 330 on the second end 329 of the sensor housing 326. In some examples, it can be appreciated that the attachment members 342 may be positioned along the sensor housing 326 such that they are distal to the framework 312. In other words, when positioned in the ostium of the left atrial appendage, the attachment members 342 may be positioned away from the framework 312 and the occlusive member 314 such that the attachment members 342 are accessible to a delivery system positioned in the left atrium.

It can be appreciated that, in some examples, after a delivery system is utilized to delivery and deploy the occlusive member 310 in the ostium of a left atrial appendage, the delivery system may be disengaged from the occlusive implant and removed from the body. Further, after removal of the delivery system, it may be desirable to cover the attachment members 342. In other words, in order to limit the attachment members 342 from potentially causing adverse effects such as device related thrombosis, it may be desirable to cover the attachment members 342 after positioning the occlusive member 310 in the ostium of the left atrial appendage. Collectively, FIGS. 6-7 illustrate an example mechanism designed to cover the attachment members 342 after positioning the occlusive member 310 in the ostium of the left atrial appendage.

FIG. 6 illustrates the that the occlusive member 310 may include a first collar 334 and a second collar 344. The first collar 334 may be similar in form and function to other collars (e.g., collar 34/134/234) described above. For example, the first collar may be fixedly engaged (e.g., fixedly attached) to the sensor housing 326 such that the collar 334 remains in a fixed position relative to the sensor housing 326 as the framework 312 is shifted between an unexpanded configuration and an expanded configuration. The first collar 334 may be fixedly attached to the sensor housing 326 using a variety of attachment techniques (e.g., glued, crimped, etc.), some of which are described above.

However, it is also contemplated that the occlusive member 310 shown in FIG. 6 may omit the first collar 334 while still preserving the functionality of the occlusive member 310 described herein. For example, in some instances the struts of the framework 312 may be directly coupled (e.g., welded) to the sensor housing 326. In other words, the sensor housing 326 may be directly integrated with any of the components (e.g., the struts) of the frame 312 using a variety of different attachment techniques.

Additionally, FIG. 6 illustrates that the framework 312 may be fixedly attached to the first collar 334. Further, FIG. 6 illustrates that the occlusive member 314 may be fixedly attached to the second collar 344. In other words, the occlusive member 314 may be fixedly attached to a portion of the framework 312 which is spaced away from the sensor housing 326 while also being unattached from the framework 312 at a location closer to the sensor housing 326. As the occlusive member 314 nears the sensor housing 326, it may separate from the framework 312 and extend to the second collar 344 whereby it may be fixedly attached, as described above.

FIG. 6 further illustrates that the second collar 344 of the occlusive member 310 may be spaced away from the first collar 334 (along the longitudinal axis of the sensor housing) such that the second collar 344 is closer to the sensor 330 than the first collar 334. Additionally, FIG. 6 illustrates that the second collar 344 may be coupled to the first collar 334 via a coil (e.g., spring) member 345 (e.g., a first end of the spring 345 may be attached to the first collar 334 while a second end of the spring 345 may be attached to the second collar 344. However, it is contemplated that, in other examples the spring 345 may include a first end attached to the sensor housing 326 and a second end attached to the second collar 344). It can be appreciated that the coil member 345 may wrap around the sensor housing 345. As will be described and illustrated in greater detail with respect to FIG. 7, it can be further appreciated that the coil member 345 may be free to elongate (e.g., translate, stretch, etc.) along the sensor housing 326. It is further contemplated that the spring 345 depicted in FIG. 6 may include a variety of different spring designs. For example, the spring 345 may include a linear spring, accordion spring, linear wave spring, an expandable mesh frame, or the like, some of which do not necessarily coil around the sensor housing 326.

FIG. 7 illustrates that the second collar 344 may be free to slide along the sensor housing 326 from a first position (depicted in dotted lines in FIG. 7 and corresponding to its initial position described above in FIG. 6), to a second position whereby the second collar 344 slides closer to the sensor 330. The direction that the second collar 344 slides along the sensor housing 326 is depicted by the arrow 346. FIG. 7 further illustrates that as the second collar 344 slides along the longitudinal axis of the sensor housing 326, it may pass over top of the attachment members 342. Because the occlusive member 314 may be attached to the second collar 344, it may also pass over top of the attachment members 342 as the second collar 344 slides over top of the attachment members 342. After passing over top of the attachment members 342, the occlusive member 314 may cover the attachment members 342, thereby reducing the possibility that the attachment members 342 cause adverse effects such as device related thrombosis.

It can be appreciated that a variety of mechanisms may be designed to "release" the second collar 344 after delivery and deployment of the occlusive member in the body. In some examples, the second collar 344 may automatically release and move proximally toward the sensor 330 with the deployment of the occlusive member from the delivery system. In other words, in some examples, the second collar 344 would release as soon as the occlusive implant was deployed out of the delivery catheter 24 (not shown in FIG. 6, but illustrated in FIG. 2). In other examples, the second collar 344 may be released via a separate mechanism. For example, the second collar 344 may be released via a rip cord, or similar mechanism. It can be further appreciated that after the second collar 344 is released, the coil 345 may expand, thereby forcing the second collar 344 to slide along the sensor housing 326 from its first position (shown in FIG. 6 and in the dotted lines in FIG. 7), to its second position (shown in FIG. 7). Additionally, after sliding along the sensor housing 326 (and over top of the attachment members 342), the second collar 344 may pull the occlusive member 314 into a taut configuration. In this configuration, the occlusive member 314 may resemble a tent-like configuration, whereby the occlusive member 314 is stretched from the second collar 344 to the framework 312 and has minimal slack.

Figure 8:
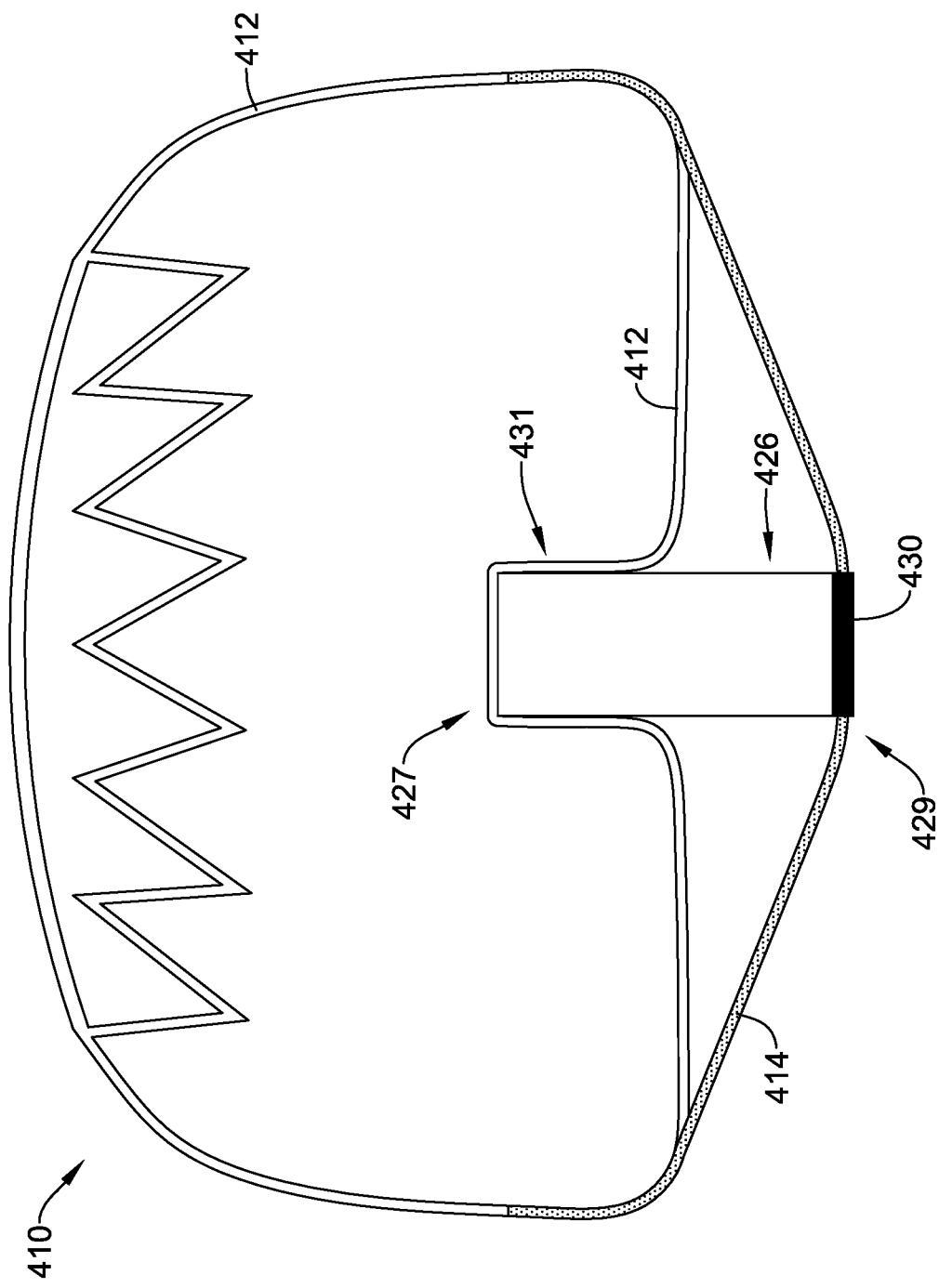
FIG. 8 is a plan view of another example occlusive implant.

FIG. 8 illustrates another medical device 410, which may be similar in form and function to the occlusive implants discussed above. For example, the medical device 410 may include an expandable framework 412 and an occlusive member 414 disposed on, disposed over, disposed about, or covering at least a portion of the expandable framework 412. The expandable framework 412 and the occlusive member 414 may be similar in form and function to the expandable framework and occlusive members described above. Additionally, in the interest of simplicity, FIG. 8 illustrates a "silhouette" of the occlusive implant 410 in an expanded configuration. It can be appreciated that the expandable framework 412 may be configured to shift between an unexpanded configuration and an expanded configuration.

FIG. 8 illustrates that the medical device 410 may further include a sensor housing 426 coupled to a collar 434. The sensor housing 426 may include a first end 427 and a second end 429 opposite the first end 427. The sensor housing 426 may further include a sensor 430 disposed along the second end 429 of the sensor housing 426. The sensor 430 and the collar 434 may be similar in form and function to other sensors described herein. For example, the sensor 430 may include a variety of different types of sensors. For example, the sensor 430 may include a pressure sensor, a temperature sensor, an oxygen sensor, or the like. Additionally, it can be appreciated that the sensor 430 (and components defining the sensor 430) may be integrated into the sensor housing 426. In some instances, the sensor 430 (and components thereof) may be fixedly attached to the second end 429 of the sensor housing. For example, the sensor 430 may be fully or partially embedded into the material used to construct the sensor housing 426.

FIG. 8 further illustrates that the expandable framework 412 may further include a frame pocket 431 which may be designed to accept the first end 427 of the sensor housing 426. In other words, the frame pocket 431 may include a geometric shape which is designed to mate with and accommodate the geometric shape of the first end 427 of the sensor housing 426. A variety of attachment techniques (e.g., glued, crimped, threaded connection, press-fit, welded, c-clamps, snap fit, over-molded, etc.), some of which are described above, may be utilized to attach the sensor housing 426 to the frame pocket 431 of the expandable framework 412. Further, FIG. 8 illustrates that the occlusive member 414 may be attached to the sensor housing 426. For example, FIG. 8 illustrates that the occlusive member 414 may be attached to a second end 429 of the sensor housing. However, this is not intended to be limiting, as it is contemplated the occlusive member 414 may be attached to any portion of the sensor housing 426. Additionally, while not illustrated in FIG. 8, it is contemplated that the occlusive member 410 shown in FIG. 8 may include a second, slidable collar (and coil member) as described above with respect to FIGS. 6-7.

Figure 9:
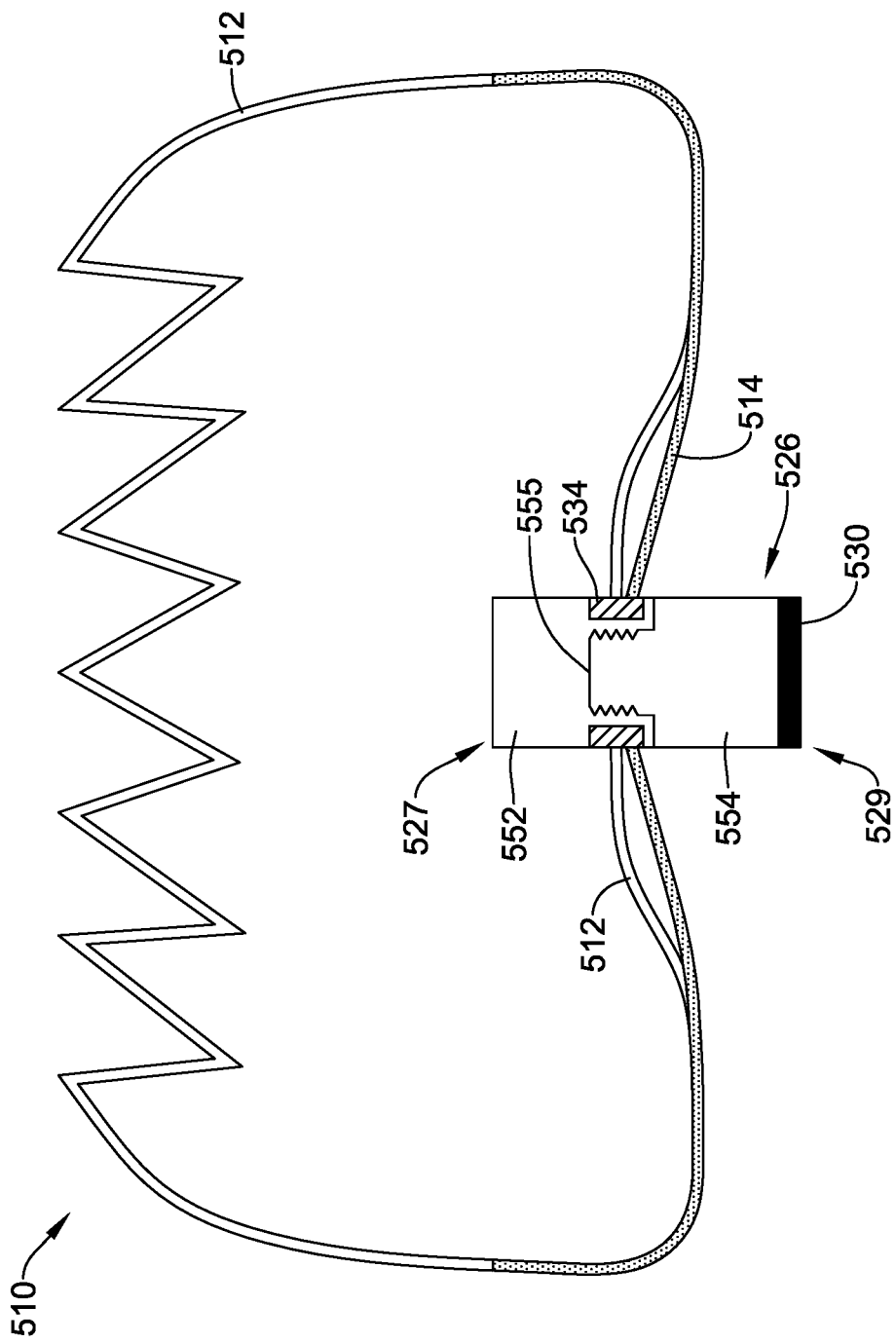
FIG. 9 is a plan view of another example occlusive implant.
Figure 10:
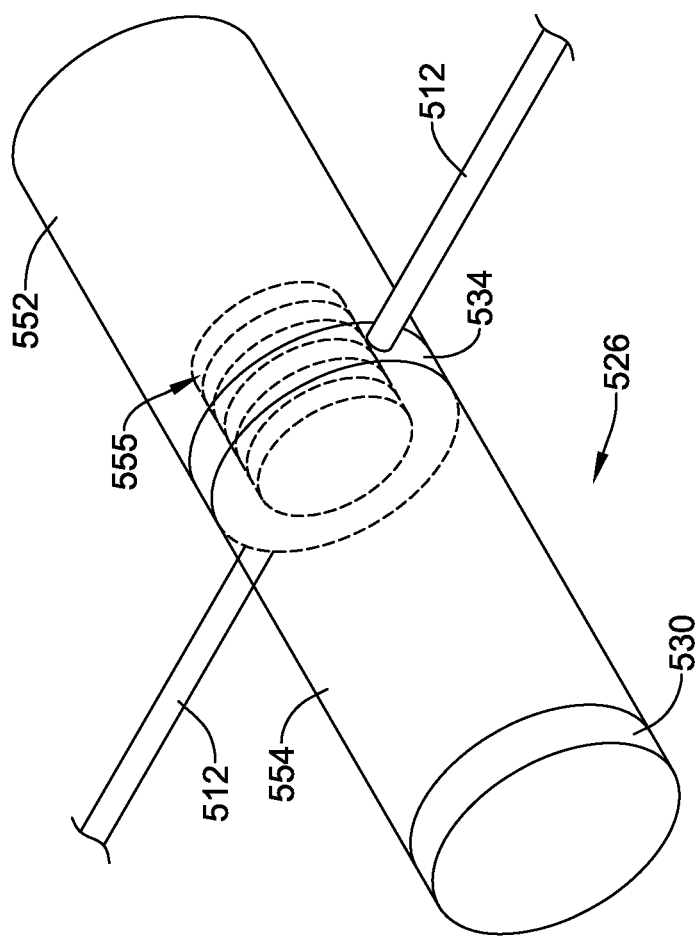
FIG. 10 is a perspective view of a portion of the example sensor shown in FIG. 9.
Figure 11:
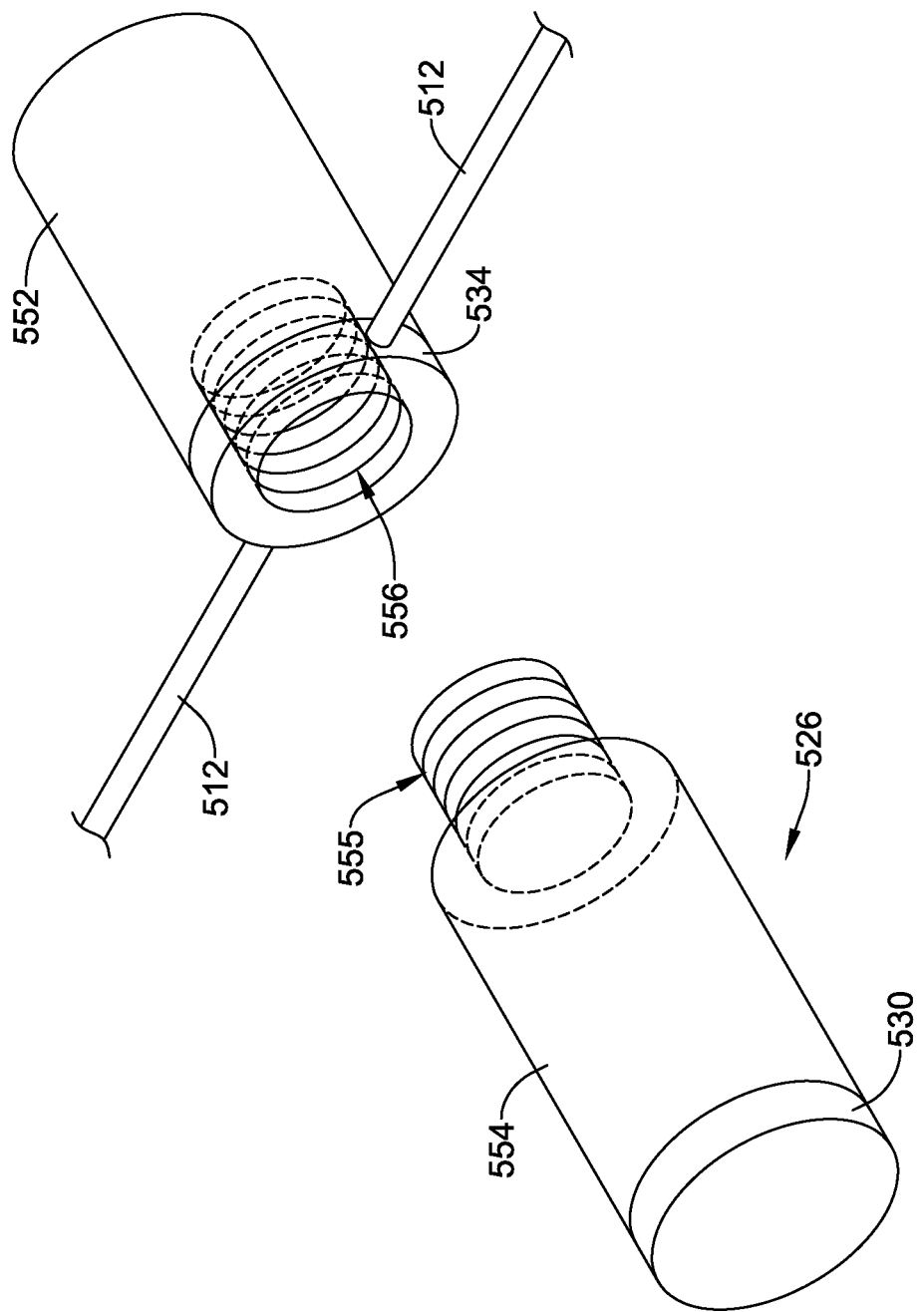
FIG. 11 is another perspective view of a portion of the example sensor shown in FIG. 9.

FIGS. 9-11 illustrates another medical device 510, which may be similar in form and function to the occlusive implants discussed above. For example, the medical device 510 may include an expandable framework 512 and an occlusive member 514 disposed on, disposed over, disposed about, or covering at least a portion of the expandable framework 512. The expandable framework 512 and the occlusive member 514 may be similar in form and function to other expandable frameworks and occlusive members described above. Additionally, in the interest of simplicity, FIG. 9 illustrates a "silhouette" of the occlusive implant 510 in an expanded configuration. It can be appreciated that the expandable framework 512 may be configured to shift between an unexpanded configuration and an expanded configuration.

FIG. 9 illustrates that the medical device 510 may further include a sensor housing 526 coupled to a collar 534. The sensor housing 526 may include a first end 527 and a second end 529 opposite the first end 527. However, as shown in FIGS. 9-11, the sensor housing 526 may include a first housing member 552 engaged with a second housing member 554. In some examples, the second housing member 554 may be threadedly engaged with the first housing member 552. In other words, the second housing member 554 may unscrewed and separated from the first housing member 552. The disengagement of the second housing member 554 from the first housing member 552 is described in greater detail with respect to FIGS. 10-11 below.

The second housing member 554 may further include a sensor 530 disposed along the second end 529 of the second housing member 554 of the sensor housing 526. For example, the sensor 530 may include a variety of different types of sensors. For example, the sensor 530 may include a pressure sensor, a temperature sensor, an oxygen sensor, or the like. Additionally, it can be appreciated that the sensor 530 (and components defining the sensor 530) may be integrated into the second sensor housing 554 of the sensor housing 526. In some instances, the sensor 530 (and components thereof) may be fixedly attached to the end of the second housing member 554 (corresponding to the second end 529 of the sensor housing 526). For example, the sensor 530 may be fully or partially embedded into the material used to construct the second housing member 554 of the sensor housing 526.

In some instances, the collar 534 may be fixedly attached to the first housing member 552 using a variety of attachment techniques. For example, the collar 534 may be weld, swaged, crimped, glued, press-fit, over-molded, threaded, etc. to the first housing member 552. Additionally, FIG. 9 illustrates that the expandable framework 512, the occlusive member 514 or both the framework 512 and the occlusive member 514 may be directly attached to the collar 534. Additionally, while FIG. 9 illustrates the collar 534 attached to the first housing member 552, it is contemplated that, in other embodiments, the collar 534 may be attached to the second housing member 554.

FIG. 10 is a perspective view of a portion of the occlusive member 510 described above. Specifically, FIG. 10 illustrates the sensor housing 526 which includes the first housing member 552 threadedly attached to the second housing member 554. FIG. 10 illustrates that the second housing member 554 may include a plurality of threads 555 which extend into and engage one or more mating threads of a cavity located in the first housing member (the cavity of the first housing member is shown in FIG. 11).

FIG. 10 further illustrates the collar 534 extending circumferentially around an outer surface of the first housing member 552. Additionally, FIG. 10 shows the struts of the expandable framework 512 directly attached to the collar 534. FIG. 10 also shows the sensor 530 positioned on the of the second housing member 554.

FIG. 11 illustrates that occlusive member 510 whereby the second housing member 554 has been disengaged from the first housing member 552. Specifically, FIG. 11 illustrates that the second housing member 554 has been unscrewed and separated from the first housing member 554. As discussed above, FIG. 11 shows the threaded cavity 556 for which the threads 555 of the second housing member 554 may extend into and threadedly engage.

While not shown in FIGS. 9-11, in some examples it is contemplated that the occlusive member 514 may be attached to the sensor housing 526 by sandwiching the occlusive member 514 between the first housing member 552 and the second housing member 554. In other words, attachment of the occlusive member 514 to the sensor housing 526 may include affixing the occlusive member 514 to a surface of the first housing member 552 and then screwing the second housing member 554 into the first housing member 552, thereby sandwiching the occlusive member 514 between eh first housing member 552 and the second housing member 554.

The materials that can be used for the various components of the occlusive implant 10 (and variations, systems or components thereof disclosed herein) and the various elements thereof disclosed herein may include those commonly associated with medical devices. For simplicity purposes, the following discussion refers to the occlusive implant 10 (and variations, systems or components disclosed herein). However, this is not intended to limit the devices and methods described herein, as the discussion may be applied to other elements, members, components, or devices disclosed herein.

In some embodiments, the occlusive implant 10 (and variations, systems or components thereof disclosed herein) may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the occlusive implant 10 (and variations, systems or components thereof disclosed herein) may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the occlusive implant 10 (and variations, systems or components thereof disclosed herein). Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the occlusive implant 10 (and variations, systems or components thereof disclosed herein) to achieve the same result.

In some embodiments, a degree of Magnetic Resonance Imaging (MM) compatibility is imparted into the occlusive implant 10 (and variations, systems or components thereof disclosed herein). For example, the occlusive implant 10 (and variations, systems or components thereof disclosed herein) and/or components or portions thereof, may be made of a material that does not substantially distort the image and create substantial artifacts (e.g., gaps in the image). Certain ferromagnetic materials, for example, may not be suitable because they may create artifacts in an MRI image. The occlusive implant 10 (and variations, systems or components disclosed herein) or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the occlusive implant 10 (and variations, systems or components thereof disclosed herein) and/or portions thereof, may be made from or include a polymer or other suitable material. Some examples of suitable polymers may include copolymers, polyisobutylene-polyurethane, polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments, the sheath can be blended with a liquid crystal polymer (LCP). For example, the mixture can contain up to about 6 percent LCP.

In some embodiments, the occlusive implant 10 (and variations, systems or components thereof disclosed herein) may include a textile material. Some examples of suitable textile materials may include synthetic yarns that may be flat, shaped, twisted, textured, pre-shrunk or un-shrunk. Synthetic biocompatible yarns suitable for use in the present disclosure include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the occlusive implant 10 (and variations, systems or components thereof disclosed herein) may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); anti-neoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

While the discussion above is generally directed toward an occlusive implant for use in the left atrial appendage of the heart, the aforementioned features may also be useful in other types of medical implants where a fabric or membrane is attached to a frame or support structure including, but not limited to, implants for the treatment of aneurysms (e.g., abdominal aortic aneurysms, thoracic aortic aneurysms, etc.), replacement valve implants (e.g., replacement heart valve implants, replacement aortic valve implants, replacement mitral valve implants, replacement vascular valve implants, etc.), and/or other types of occlusive devices (e.g., atrial septal occluders, cerebral aneurysm occluders, peripheral artery occluders, etc.). Other useful applications of the disclosed features are also contemplated.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. An occlusive implant, comprising:
an expandable framework configured to shift between a collapsed configuration and an expanded configuration;
an occlusive member disposed along at least a portion of the expandable framework;
a first collar attached to the expandable framework;
a sensor housing coupled to the first collar, the sensor housing having a first end and a second end opposite the first end;
a second collar slidably disposed along an outer surface of the sensor housing, wherein the second collar is coupled to the expandable framework via a spring; and
a sensor disposed along the second end of the sensor housing;
wherein elongation of the spring is configured to shift the second collar from a first position in which the second collar is adjacent the first collar to a second position in which the second collar is adjacent the sensor;
wherein the spring is configured to shift the second collar from the first position to the second position while the expandable framework remains in the expanded configuration.

2. The occlusive implant of claim 1, wherein the spring is wrapped around the outer surface of the sensor housing.

3. The occlusive implant of claim 1, wherein the spring includes a first end coupled to the first collar and a second end coupled to the second collar.

4. The occlusive implant of claim 1, wherein the spring includes a first end coupled to the sensor housing and a second end coupled to the second collar.

5. The occlusive implant of claim 1, wherein the first collar includes an aperture, and wherein the sensor housing extends within the aperture of the first collar.

6. The occlusive implant of claim 5, wherein the first collar extends circumferentially around the outer surface of the sensor housing.

7. The occlusive implant of claim 1, wherein the first collar and the expandable framework are formed from a monolithic sheet of material.

8. The occlusive implant of claim 1, wherein the expandable framework further includes a plurality of struts attached to the first collar.

9. The occlusive implant of claim 1, wherein the expandable framework further includes a plurality of struts attached to the sensor housing.

10. The occlusive implant of claim 1, wherein the first collar is configured to remain stationary relative to the sensor housing while the expandable framework shifts between the collapsed configuration and the expanded configuration.

11. The occlusive implant of claim 1, wherein the first collar is configured to remain stationary relative to the sensor housing while the second collar shifts along the outer surface of the sensor housing.

12. The occlusive implant of claim 1, wherein the sensor is positioned within the expandable framework such that the sensor faces away from the occlusive member.

13. The occlusive implant of claim 1, wherein a first portion of the occlusive member is attached to the expandable framework and a second portion of the occlusive member is attached to the second collar.

14. The occlusive implant of claim 1, wherein the sensor housing includes a series of apertures configured to attach to a delivery device, the series of apertures being spaced toward the first end of the sensor housing relative to the sensor.

15. The occlusive implant of claim 14, wherein when the second collar is in the second position, the occlusive member covers the series of apertures.

16. An occlusive implant, comprising:
an expandable framework configured to shift between a collapsed configuration and an expanded configuration, the expandable framework including a plurality of struts spaced around a longitudinal axis of the expandable framework;
an occlusive member disposed along at least a portion of the expandable framework;
a first collar attached to the plurality of struts of the expandable framework, the first collar defining an aperture, where a central region of the aperture is aligned with the longitudinal axis of the expandable framework;
a sensor housing coupled to the first collar and extending along the longitudinal axis of the expandable framework through the occlusive member, the sensor housing having a first end and a second end opposite the first end;
a second collar slidably disposed along an outer surface of the sensor housing, wherein the second collar is coupled to the expandable framework via a spring and the second collar is fixedly attached to the occlusive member; and
a sensor disposed along the second end of the sensor housing;
wherein elongation of the spring is configured to shift the second collar longitudinally along the sensor housing from a first position in which the second collar is closer to the first end of the sensor housing than the second end of the sensor housing to a second position in which the second collar is closer to the second end of the sensor housing than the first end of the sensor housing.

17. The occlusive implant of claim 16, wherein the spring is wrapped around the outer surface of the sensor housing.

18. The occlusive implant of claim 16, wherein the spring includes a first end coupled to the first collar and a second end coupled to the second collar.

19. The occlusive implant of claim 16, wherein the first collar is configured to remain stationary relative to the sensor housing while the second collar shifts along the outer surface of the sensor housing.

20. An occlusive implant, comprising:
an expandable framework configured to shift between a collapsed configuration and an expanded configuration;
an occlusive member disposed along at least a proximal portion of the expandable framework;
a first collar attached to the expandable framework, the first collar defining an aperture coaxial with a longitudinal axis of the expandable framework;
a sensor housing disposed within the aperture, coupled to the first collar, and extending along the longitudinal axis of the expandable framework, the sensor housing having a first end disposed distal of the occlusive member and a second end disposed proximal of the occlusive member;
a second collar fixedly attached to the occlusive member, the second collar being slidably disposed along an outer surface of the sensor housing proximal of the first collar, wherein the second collar is coupled to the first collar via a spring disposed about the sensor housing; and a sensor disposed along the second end of the sensor housing;

wherein elongation of the spring is configured to shift the second collar longitudinally along the sensor housing from a first position in which less than half of the sensor housing is disposed distal of the occlusive member to a second position in which more than half of the sensor housing is disposed distal of the occlusive member.

\* \* \* \* \*